(12) United States Patent
Kong

(10) Patent No.: US 12,103,813 B2
(45) Date of Patent: Oct. 1, 2024

(54) REEL WITH AUTOMATIC LINE EXTENSION

(71) Applicant: William Kong, Santa Clara, CA (US)

(72) Inventor: William Kong, Santa Clara, CA (US)

( * ) Notice: Subject to any disclaimer, the term of this patent is extended or adjusted under 35 U.S.C. 154(b) by 289 days.

(21) Appl. No.: 17/852,166

(22) Filed: Jun. 28, 2022

(65) Prior Publication Data

US 2022/0332539 A1    Oct. 20, 2022

Related U.S. Application Data

(63) Continuation-in-part of application No. 17/137,210, filed on Dec. 29, 2020, now Pat. No. 11,608,245.

(51) Int. Cl.
*B65H 75/44* (2006.01)
*A61M 39/08* (2006.01)

(52) U.S. Cl.
CPC ..... *B65H 75/4484* (2013.01); *B65H 75/4486* (2013.01); *A61M 39/08* (2013.01); *A61M 2039/087* (2013.01); *B65H 2553/20* (2013.01)

(58) Field of Classification Search
CPC  B65H 75/44; B65H 75/4478; B65H 75/4484; B65H 75/4486; B65H 2701/33
See application file for complete search history.

(56) References Cited

U.S. PATENT DOCUMENTS

| | | | |
|---|---|---|---|
| 1,982,619 A | 11/1934 | Harris | |
| 2,777,646 A | 1/1957 | Manahan | |
| 7,104,491 B2 | 9/2006 | Vinding | |
| 10,576,236 B2 | 3/2020 | Davison | |
| 11,608,245 B2 * | 3/2023 | Kong | B65H 75/4486 |
| 2006/0243282 A1 | 11/2006 | Sackman | |
| 2010/0307496 A1 | 12/2010 | Lueckenhoff | |
| 2011/0011401 A1 | 1/2011 | Skovgard | |
| 2011/0017856 A1 | 1/2011 | Penn | |
| 2014/0166799 A1 | 6/2014 | Davis et al. | |
| 2015/0069164 A1 | 3/2015 | Moore | |
| 2016/0060075 A1 | 3/2016 | Slowik | |
| 2016/0354570 A1 | 12/2016 | Arroyo | |
| 2017/0239011 A1 | 8/2017 | Lucas | |

* cited by examiner

*Primary Examiner* — Sang K Kim
(74) *Attorney, Agent, or Firm* — GSS Law Group; Gregory S. Smith; Phillip M. Wagner

(57) ABSTRACT

An automatic line reel includes a flexible line wound onto a motor-driven reel assembly. A processor controlling the motor detects contact pressure between the flexible line and a triangular pressure transducer, automatically extending the flexible line when the contact pressure exceeds a preset threshold. Line extension stops when contact pressure falls below a second preset threshold. The flexible line may be retracted and rewound around the reel assembly by activation of a switch on a wireless remoted control, by a switch on the automatic line reel, or by activation of a smart phone application program in data communication with the processor controlling the reel assembly. A reel assembly is optionally configured to maintain uninterrupted fluid communications through the automatic line reel as the reel assembly rotates. The reel assembly may optionally be configured to maintain uninterrupted electrical signal communication through the automatic line reel.

9 Claims, 20 Drawing Sheets

Partial Cross-Section A-A

Partial Cross-Section A-A

Alternative View A

Alternative View A

REEL WITH AUTOMATIC LINE EXTENSION

FIELD OF THE INVENTION

Embodiments are related to rotatable reels for carrying flexible lines such as hose and electrical cables.

BACKGROUND

A person receiving respiratory assistance from an oxygen supply such as an oxygen concentrator or an oxygen bottle may wear a mask or nasal cannula attached to the oxygen supply by a hose. A substantial length of hose may be provided to enable the person to move about in the vicinity of the oxygen supply. The person's range of movement may be limited by the length of the hose between the mask or cannula and the oxygen supply. Moving beyond the length of the fully extended hose may require moving the oxygen supply or disconnecting the hose and reconnecting a longer hose.

Some oxygen supplies are sufficiently portable to enable the equipment to be easily relocated. Whether the oxygen supply is moved or the person moves relative to the oxygen supply, slack in the hose may accumulate in loops or bights where a person desires to walk. A kink, twist, or tangle may form in the hose from the hose being pulled and relaxed as the person moves about, possibly restricting the flow of oxygen through the hose and possibly damaging the hose, particularly if the hose is made from unreinforced flexible tubing or has a relatively small outer diameter, as may be found in some equipment providing respiratory oxygen. Hose connecting a person to an oxygen supply may present a tripping hazard, especially for someone with impaired balance. A person tripping over the hose may fall or put enough tension on the hose to break the hose or disconnect the hose from the oxygen supply. Someone who is unwell or distracted may forget to move the slack hose or the oxygen supply and may stumble over the hose. A person may step on the hose or roll a wheelchair or cart over the hose, possibly damaging the hose or shutting off the flow of gas through the hose.

A person may be connected by a flexible line to an instrument or fluid reservoir for reasons other than respiratory support. For example, an ambulatory patient in a hospital may wear electrodes or intravenous ports connected by flexible lines such as a hose and/or electrical conductors to a supply vessel for a therapeutic or diagnostic liquid, a monitoring instrument on a cart or mobile stand, a syringe or bag for intravenous medication, a vessel for collecting drainage from a surgical site, a urinary catheter, and so on. For each of these examples, it is preferable that excess slack line not accumulate where a person could trip on the line, and that the flexible line be protected from kinking and mechanical damage.

Some previous solutions for reducing slack in a flexible line have coupled a torsion spring to a reel to retract a line extended from the reel. The line may retract automatically when the spring force exceeds tension in the line, allowing the spring to turn the reel and wind the line onto the reel. Such devices may be effective for preventing the accumulation of slack in the line, but may put the line under sufficient tension that a person catching a limb, a crutch, or a walker against the line may stumble and fall. A spring force sufficient to turn a reel and remove slack from the line may cause the line to pull uncomfortably against the person, for example when the line is connected to a nasal cannula, a surgical port, or an electrode attached to a person's skin. The spring may pull continuously against the line, whether the person and line are at rest or moving.

Other devices have a reel driven in rotation by a motor, with a direction of rotation and possibly a rate of rotation of the reel controlled by manually-operated switches. A person wearing a device connected to flexible line wound onto the reel may forget to operate the switches to extend the cable or remove slack from the line. The person may lack sufficient manual dexterity or situational awareness to operate the switches or stop rotation of the reel before the line is placed under too much tension. Abruptly reaching the end of travel imposed by the length of the line or the force of line retraction may cause the person to lose balance or impair the connection between the person and the line.

Previous solutions for motor-driven reels and spring-driven reels may be configured for holding a preferred length of flexible line. When the flexible line is damaged and subsequently replaced, it may be possible to attach a line that is too short or too long compared to the preferred length. A line that is too long may not be retracted sufficiently to eliminate slack line outside the reel, possibly allowing slack line to accumulate and present a trip hazard. A line that is too short may pull uncomfortably or unsafely against a person connected to the line.

SUMMARY

Example apparatus embodiments of an automatic line reel include a base unit; a motor attached to the base unit; and a reel assembly coupled to the motor. The reel assembly includes a reel drum; a reel hub connected to the reel drum with the reel hub and the reel drum rotatable together by the motor; and a reel axle slidably engaged with a hub end aperture formed in the reel hub. The reel axle is preferably affixed to the base unit so as to prevent rotation of the reel axle during rotation of the reel hub.

The base unit further includes a processor electrically connected to the motor; and a triangular pressure transducer attached to the base unit and electrically connected to the processor. The triangular pressure transducer includes a first side wall; a second side wall joined to the first side wall; a third side wall joined to the first side wall and the second side wall with a transducer void space formed between the first side wall, the second side wall, and the third side wall; and a flat pressure sensor attached to the first side wall inside the transducer void space, the flat pressure sensor electrically connected to the processor.

The base unit includes an outer enclosure. In some embodiments, the base unit includes a fixed reel cover attached to the outer enclosure; a removable reel cover removably attached to the outer enclosure; and the reel axle attached to the removable reel cover. In some embodiments the fixed reel cover is an integrally-formed part of the outer enclosure.

Example embodiments of the base unit further include a hub connector attached to the reel hub; a stationary line connector attached to the reel axle; a stationary line attached to the stationary line connector; and an extendable line passing through the transducer void space, around the reel drum, and connected to the hub connector.

Example automatic line reel embodiments optionally include the reel axle formed with an axle void space and a fluid aperture in fluid communication with the axle void space; the reel hub formed with a hub sidewall aperture; a hub plenum formed between the reel axle and the reel hub; an O-ring surrounding the reel axle and interposed between the reel axle and the reel hub; and the hub connector in fluid communication with the stationary line connector through the hub sidewall aperture, the hub plenum, the fluid aperture, and the axle void space. The extendable line preferably remains in uninterrupted fluid communication with the stationary line while the reel assembly is driven in rotation by the motor.

The example automatic line reel optionally includes the reel axle having a circumferential conductor positioned on an outer surface of the reel axle; a spring contact pin passing through a side wall of the reel hub, with the spring contact pin positioned to contact the circumferential conductor; a first electrical connector electrically connected to the spring contact pin; a second electrical connector attached to the stationary line connector; and an electrical conductor connecting the second electrical connector and the circumferential conductor. The extendable line preferably remains in uninterrupted electrical communication with the stationary line while the reel assembly is driven in rotation by the motor.

An automatic line reel optionally includes more than one reel assembly. A first reel assembly includes a first reel axle and a first reel hub, with the first reel assembly configured for establishing an uninterrupted fluid path through the first reel axle and the first reel hub. A second reel assembly includes a second reel axle and a second reel hub, with the second reel assembly configured for establishing an uninterrupted electrical signal path through the second reel axle and the second reel hub, and the first reel assembly and the second reel assembly are interchangeably connectable to the motor.

An alternative example apparatus embodiment includes an outer enclosure having a bottom panel, four side walls extending upward from the bottom panel, and an enclosure cover removably attached to the side walls; a fixed reel cover attached to the bottom panel in a space between the side walls, the bottom panel, and the enclosure cover; and a motor having a motor drive shaft rotatable about an axis of rotation, with the motor attached to the outer enclosure with the axis of rotation perpendicular to the bottom panel. The example apparatus embodiment further includes a reel assembly positioned within the fixed reel cover. The reel assembly includes a reel drum configured for connection to the motor drive shaft; a reel flange attached to the reel drum with the reel flange extending radially outward from the axis of rotation; and a reel hub attached to the reel drum. The reel hub includes a stationary swivel union tube held stationary relative to the outer enclosure and a swivel union block rotatably joined to the stationary swivel union tube with the swivel union block attached to the reel drum, and with the reel drum, the reel flange, and the swivel union block rotatable together about the axis of rotation by the motor; and a triangular pressure transducer attached to the outer enclosure in the space between the four walls. The triangular pressure transducer includes a first transducer side wall; a second transducer side wall joined to the first transducer side wall; a third transducer side wall joined to the first transducer side wall and the second transducer side wall with a transducer void space formed between the first transducer side wall, the second transducer side wall, and the third transducer side wall; a sensor mounting surface formed parallel to the third transducer side wall inside the transducer void space opposite the third transducer side wall, with the sensor mounting surface extending from the first transducer side wall to the second transducer side wall; and a pressure sensor attached to the sensor mounting surface.

The alternative example apparatus embodiment optionally includes the triangular pressure transducer positioned in the outer enclosure with the sensor mounting surface parallel to the bottom panel. The example triangular pressure transducer optionally further includes a second pressure sensor attached to the first transducer side wall inside the transducer void space; and a third pressure sensor attached to the second transducer side wall inside the transducer void space.

The alternative example apparatus embodiment optionally further includes a first tubing connector connected for fluid communication with the swivel union block; a second tubing connector attached to the outer enclosure; and a stationary pipe elbow. The stationary pipe elbow includes a hollow elongated segment connected for fluid communication with the second tubing connector; and a hollow short segment extending at a right angle from the elongated segment, with the short segment connected for fluid communication with the swivel union tube, wherein the stationary pipe elbow holds the stationary swivel union tube stationary with respect to the outer enclosure.

DESCRIPTION

Figure 1:
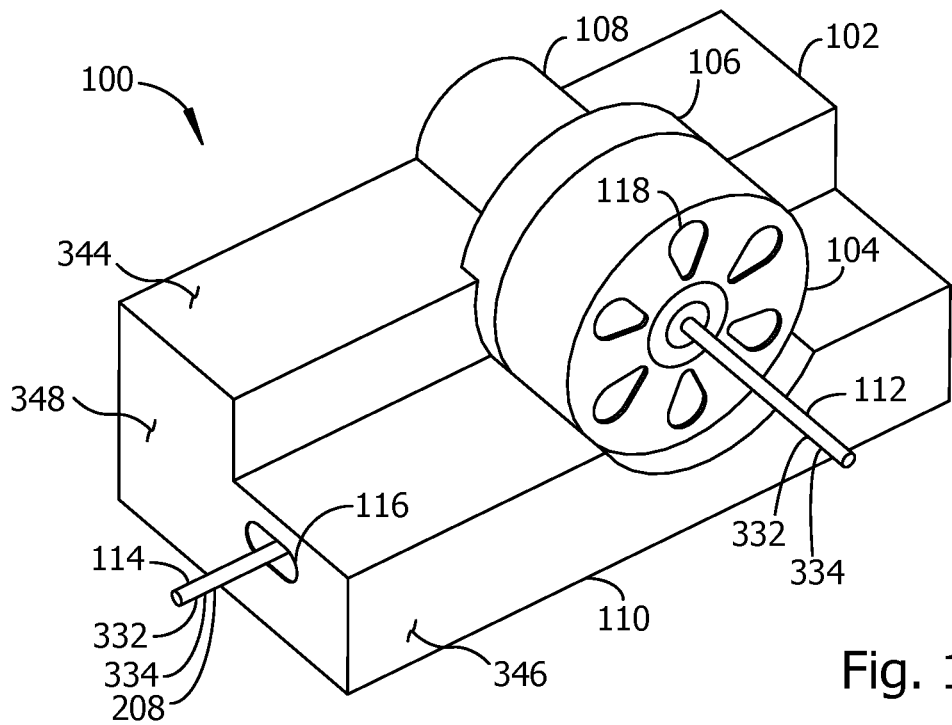
FIG. 1 is a pictorial view of an example embodiment of an automatic line reel.

An apparatus embodiment referred to herein as an automatic line reel is configured for preventing the accumulating of unwanted slack in a flexible line extendable from and retractable into the automatic line reel. Embodiments of the automatic line reel include a base unit having a reel assembly rotatably driven by a motor under control of a processor. The processor directs the motor to rotate the reel assembly to extend the flexible line in response to detection of sufficient contact pressure between the line and a triangular pressure transducer inside the base unit. The processor directs the motor to retract the flexible line and wind the line onto the reel assembly in response to activation of a switch by a person using the apparatus. The processor stops rewinding the flexible line when the line exerts sufficient contact pressure against the triangular pressure transducer, preventing the line from pulling uncomfortably against the person.

The disclosed example embodiments are effective for preventing slack line from accumulating and creating a tripping hazard for a person moving about while connected to the automatic line reel by the flexible line, and for reducing discomfort caused by tension in the flexible line pulling against the person. The reel assembly and other parts in the base unit are covered by an outer enclosure to prevent contact between moving parts inside the apparatus and persons nearby, for example the person using the automatic line reel or another person nearby such as a caregiver or a child.

The triangular pressure transducer included with embodiments of the automatic line reel is configured for quickly and accurately detecting an increase in tension in the flexible line, for example when a person pulls against the line or comes into inadvertent contact with the line with sufficient force to cause a tripping hazard or damage the automatic line reel. The flexible line passes through a void space between three flat walls forming a support frame of the triangular pressure transducer. The three walls encourage the flexible line to move into contact with one or more pressure sensors positioned to detect when the flexible line is being pulled (placed in tension) from many different directions relative to the longitudinal axis of the triangular pressure transducer. The flexible line may be placed in tension, for example, when a person wearing a device to which the flexible line is attached moves away from the automatic line reel, when a person grips the flexible line with a hand and pulls on the flexible line, or when a person moving about inadvertently catches a limb, trolley, wheelchair, or support appliance against the line.

When a magnitude of contact pressure between the flexible line and the triangular pressure transducer exceeds a first pressure threshold value stored in a memory in data communication with the processor, the processor activates the motor to rotate the reel assembly and unwind the flexible line, extending the flexible line outward from the automatic line reel and increasing the distance a person connected to the flexible line may move away from the automatic line reel. The processor continues to rotate the reel assembly as long as contact pressure between the flexible line and the triangular pressure transducer exceeds the first pressure threshold, and for a short time after the contact pressure is reduced, allowing a small amount of slack to form in the flexible line extending from the apparatus. The small amount of slack prevents the flexible line from pulling uncomfortably against the person connected to the line while the person remains in one location. When the processor stops reel rotation, the amount of slack line is preferably not enough to form a loop, pile, or tangle of slack line on a floor, table, bed, or chair.

After the processor stops the rotation of the reel assembly, another pull against the line causes more line to extend, up to a line length limit stored in memory. The line length limit is optionally shorter than the overall length of the extendable line to allow for at least one full turn of line to remain on the reel assembly, providing strain relief to the line and line connections. The processor controls reel rotation to prevent all of the flexible line from being withdrawn from the reel, stopping the reel before the line can be disconnected from the reel assembly. The processor optionally counts rotations of the reel assembly to determine a length of line extended from the reel assembly and a length of line remaining on the reel assembly. The extendable line wound around the reel assembly optionally includes a line stop attached to the line, with the line stop positioned to activate a pressure sensor as the line stop moves through the triangular pressure transducer. Upon detection of sufficient contact pressure between the line stop and the pressure sensor, the processor stops rotation of the reel assembly.

An automatic line reel including one or more line stops optionally omits components needed to count reel rotations. Whether the processor counts reel rotations or detects contact between the triangular pressure transducer and a line stop, stopping rotation of the reel assembly before full extension of the flexible line prevents unintentional disconnection of the flexible line from the reel assembly, prevents interruption of fluid flow in flexible lines configured for fluid transmission, and prevents interruption of electrical signals in flexible lines configured for electrical signal transmission.

An automatic line reel is optionally provided with a lightweight, portable remote control device commanding the processor in the base unit to retract the line and wind the flexible line around the reel assembly. Line retraction may also be initiated from a switch on the base unit. After line retraction is initiated, the processor continues to direct the reel assembly to retract the flexible line until the line contacts the triangular pressure transducer with sufficient force to exceed a second pressure threshold. Upon detection of line contact pressure above the second pressure threshold, the processor stops rotation of the reel assembly. In some apparatus embodiments, the remote control device includes an electrical switch for activating retraction of the flexible line and a wireless communications transceiver configured to communicate a state of the switch to the processor controlling the reel assembly. In other embodiments, the remote control device is implemented as an applications program configured for execution on a smart phone, for example a cellular telephone having a touch input display and a wireless data communications transceiver capable of communicating with the processor in the automatic line reel.

The processor is configured to extend and retract the flexible line at about the linear rate of travel of a person walking, corresponding to a rate of extension and/or retraction in a range from about 0.5 meter/sec to about 2.5 meter/sec. Extending and retracting the flexible line at about the same speed a person moves about reduces uncomfortable tugging and pulling on the line against a person connected to the flexible line, and reduces accumulation of excess slack in the flexible line. Recalibrating the processor for different lengths or types of flexible line, for example after a worn or damaged line is replaced or a reel assembly configured for fluid connections is replaced with a reel assembly configured for electrical connections, is easily performed by a person using the apparatus.

Embodiments of the automatic line reel are effective for reducing a tripping hazard caused by the flexible line. Should an object such as a person's leg or foot, a cane, a crutch, a walker, or part of a wheelchair contact the flexible line with sufficient force for the triangular pressure transducer output signal to exceed a third pressure threshold, the processor quickly commands the motor assembly to rapidly unwind line from the reel, thereby reducing contact force between the flexible line and the object. The rapid extension of the line in response to contact pressure detection in excess of the third pressure threshold reduces the effects of unexpected contact on a person's balance, possibly preventing the person from tripping over the line and possibly protecting the line from damage.

A reel assembly configured for establishing an uninterrupted fluid path through the automatic line reel is included with some embodiments of the automatic line reel. Another reel assembly configured for establishing an uninterrupted electrical signal path through the automatic line reel is optionally provided in addition to, or alternatively instead of, the reel assembly configured for fluid connections. The reel assembly configured for establishing an uninterrupted fluid path and the reel assembly configured for establishing an uninterrupted electrical signal path are preferably interchangeably connectable to the motor in the automatic line reel.

Figure 2:
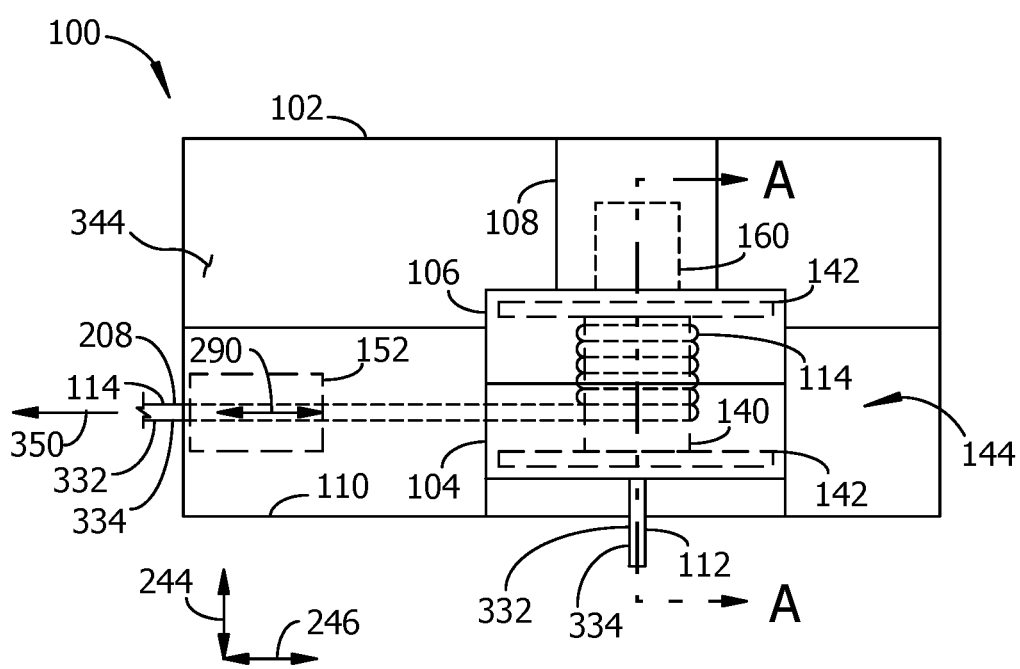
FIG. 2 is a view toward a top side of the example embodiment of FIG. 1.

An example apparatus embodiment 100 referred to herein as an automatic line reel 100 is shown in FIG. 1 as a pictorial view toward a top side 344, a transverse side 348, and a longitudinal side 346 of a base unit 110 having an outer enclosure 102. The example automatic line reel 100 is shown in FIG. 2 as a view toward the top side 344, and in FIG. 3 as a view toward the longitudinal side 346 with a removable reel cover 104 omitted from the figure. The automatic line reel 100 is operable to selectively extend and retract an extendable line 114 in a longitudinal direction 246 through a first line aperture 116 formed in the transverse side 348 of the base unit 110. The extendable line 114 is wound onto rotatable parts of a reel assembly 144 positioned behind the removable reel cover 104 and a fixed reel cover 106. Vent apertures 118 may be formed in the removable reel cover 104 and optionally in other parts of the outer enclosure 102. The reel covers (104, 106) and other parts of the outer enclosure remain stationary, i.e., do not rotate during rotation of the reel assembly. A stationary line 112 attaches to a stationary line connector 126 attached to a reel axle 122. The reel axle 122 is a nonrotating component of the reel assembly 144, and like the fixed reel cover 106 and removable reel cover 104 forming part of the outer enclosure 102, the reel axle and stationary line do not rotate or twist when the reel assembly rotates inside the base unit 110. Eliminating twisting and rotation of the stationary line 112 prevents kinking in the stationary line and facilitates uninterrupted fluid flow through the stationary line, reel assembly, and extendable line.

The extendable line 114 is an example of a flexible line 208 configured for coupling the automatic line reel 100 to a person using the apparatus. The stationary line 112 may optionally be made from the same materials as the flexible line 208. An automatic line reel may selectively be configured to carry a flexible line adapted for carrying a fluid or a flexible line adapted for carrying electrical signals. Because the stationary line 112 does not rotate or twist while the flexible line 208 is extended or retracted from the automatic line reel 100, the stationary line 112 may optionally be made from materials that are substantially less flexible than the extendable line 114. For an automatic line reel 100 configured for establishing an uninterrupted fluid connection between a fluid reservoir and a person, a hose 332 is an example of the flexible line 208. As used herein, a hose 332 refers to a flexible hollow tube and a pipe refers to a rigid hollow tube. When fluid connections are to be established through the automatic line reel 100, the extendable line 114 is therefore preferably a hose, and the stationary line 112 may alternatively be a hose or a pipe as needed. Examples of applications of the automatic line reel in which fluid connections are to be established include, but are not limited to, supplying respiratory gas mixtures to a person, coupling an ostomy site to a waste bag, drainage of a surgical site, coupling a urinary catheter to a waste collection bag, and coupling fluids to be delivered intravenously to a surgical port.

When uninterrupted electrical connections are to be established through the automatic line reel 100, the extendable line 114 and/or the stationary line 112 may be implemented as electrical cables 334 having one or more electrical conductors. As used herein, an uninterrupted electrical connection refers to a continuous flow of electric current. Examples of applications of the automatic line reel in which uninterrupted electrical connections are to be established include, but are not limited to, connection of electrodes for monitoring electrical signals from a person' heart, nervous system, or muscles, connection of sensors for monitoring respiration or blood pressure, and connection of electrodes for stimulation of muscles or other tissues.

Figure 3:
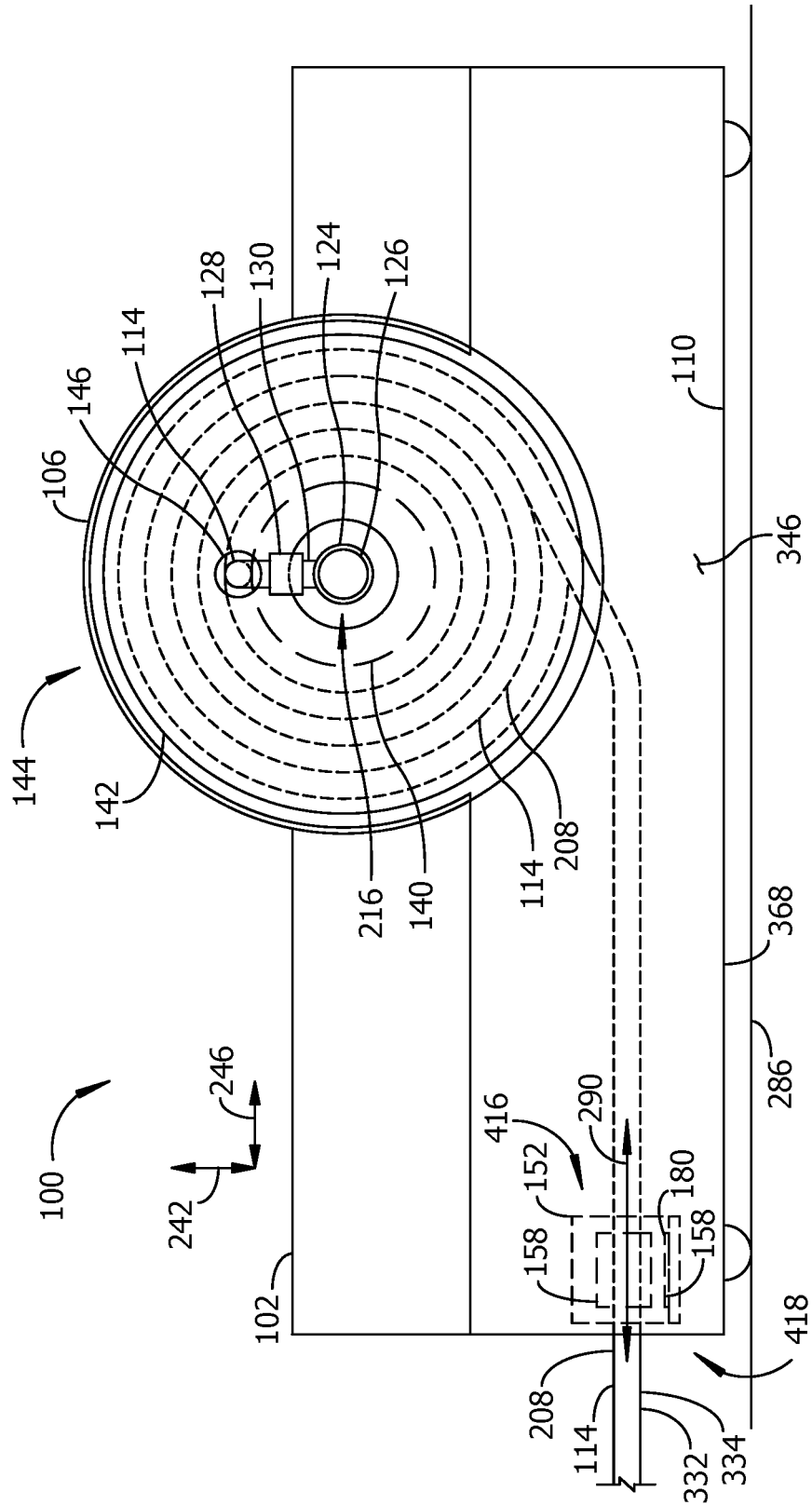
FIG. 3 is a view toward a longitudinal side of the example embodiment of FIG. 1.
Figure 10:
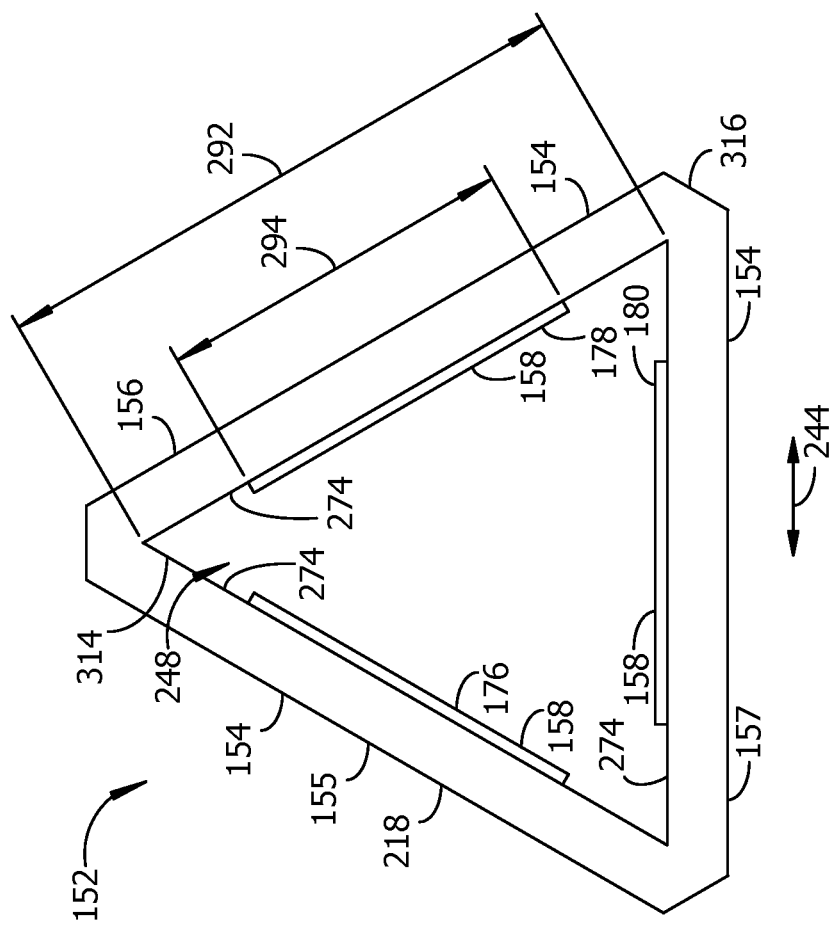
FIG. 10 is an end view of the example triangular pressure transducer of FIGS. 8-9, illustrating an example pressure transducer with three pressure sensors.

As suggested in the examples of FIGS. 2 and 3, the extendable line 114 passes through the first line aperture 116, into the outboard end 418 of the triangular pressure transducer 152, out the inboard end 416 of the triangular pressure transducer, and is wound onto the reel assembly 144. The first line aperture 116 is formed in the outer enclosure 102 of the base unit 110. In the example of FIG. 1, the first line aperture 116 is formed with an obround perimeter. The first line aperture 116 may alternately be formed with a triangular perimeter about the same size as a triangular hollow structure 314 (ref. FIG. 10) forming part of the triangular pressure transducer. The triangular pressure transducer 152 is preferably attached to the base unit 110 with a longitudinal axis 290 of the triangular pressure transducer approximately parallel to a direction of line extension 350 through the first line aperture 116. The example arrangement of the longitudinal axis 290 parallel to the direction of extension 350 minimizes contact forces between the extendable line 114 and a pressure sensor inside the triangular pressure transducer 152 while the line is moving in an approximately perpendicular direction 350 from the transverse side 348 of the automatic line reel 100, avoiding unintentional interruption of line extension by unwanted activation of the triangular pressure transducer.

The example reel assembly 144 in FIGS. 2-7 includes two reel flanges 142 joined to opposite ends of a reel drum 140. The extendable line 114 wraps around the reel drum 140 between the opposing reel flanges 142. The reel assembly 144 is driven in rotation by a motor 160 attached to the base 110. A motor cover 108 prevents accidental contact with the motor 160 and provides protection against spilled fluids. The motor cover 108 is optionally an integrally-formed part of the outer enclosure 102 or may alternatively be formed as a separable part of the outer enclosure. The motor cover 108 protects the motor from dust and spills and prevents accidental contact with internal parts of the apparatus by a person using the automatic line reel 100.

The reel assembly 144 is positioned within a void space 212 formed by the fixed reel cover 106, the removable reel cover 104, and the outer enclosure 102 of the base unit 110. The reel assembly 144 rotates about an axis of rotation 214 passing through a rotational center of the motor drive shaft 162. The motor drive shaft 162 engages a drive shaft connector 206 on the reel assembly 144. The drive shaft connector 206 holds securely to the motor drive shaft 162 to prevent slippage between the reel assembly and the motor drive shaft. The drive shaft connector 206 is optionally configured to permit easy removal and replacement of the reel assembly 144, for example to replace a damaged or worn reel assembly or to replace a reel assembly configured for electrical connections with a reel assembly configured for fluid connections.

Figure 4:
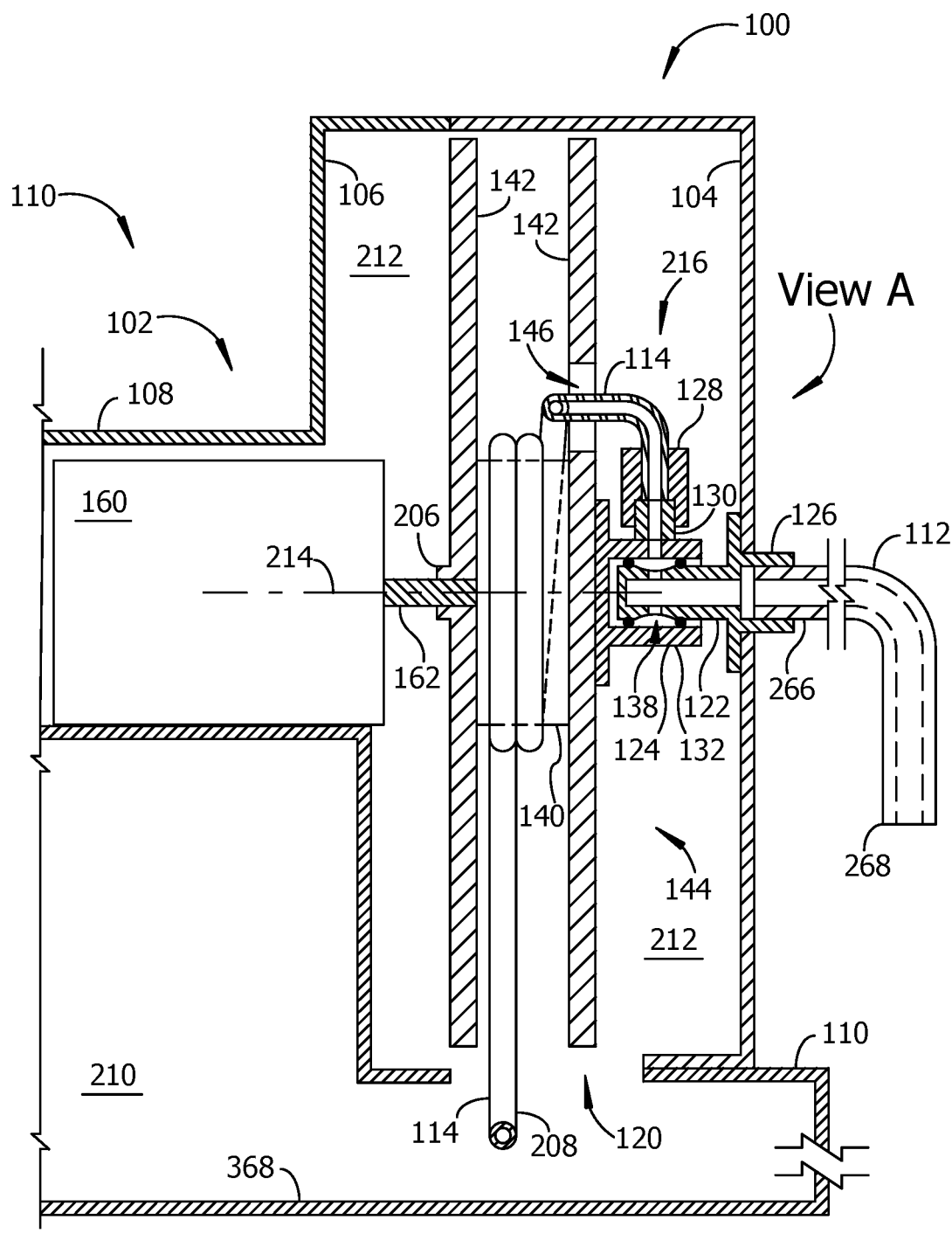
FIG. 4 is a schematic diagram representing a partial cross-sectional view A-A of the example automatic line reel of FIGS. 1-3. A location and viewing direction for the cross-sectional view is marked by a section line A-A in FIG. 2.
Figure 5:
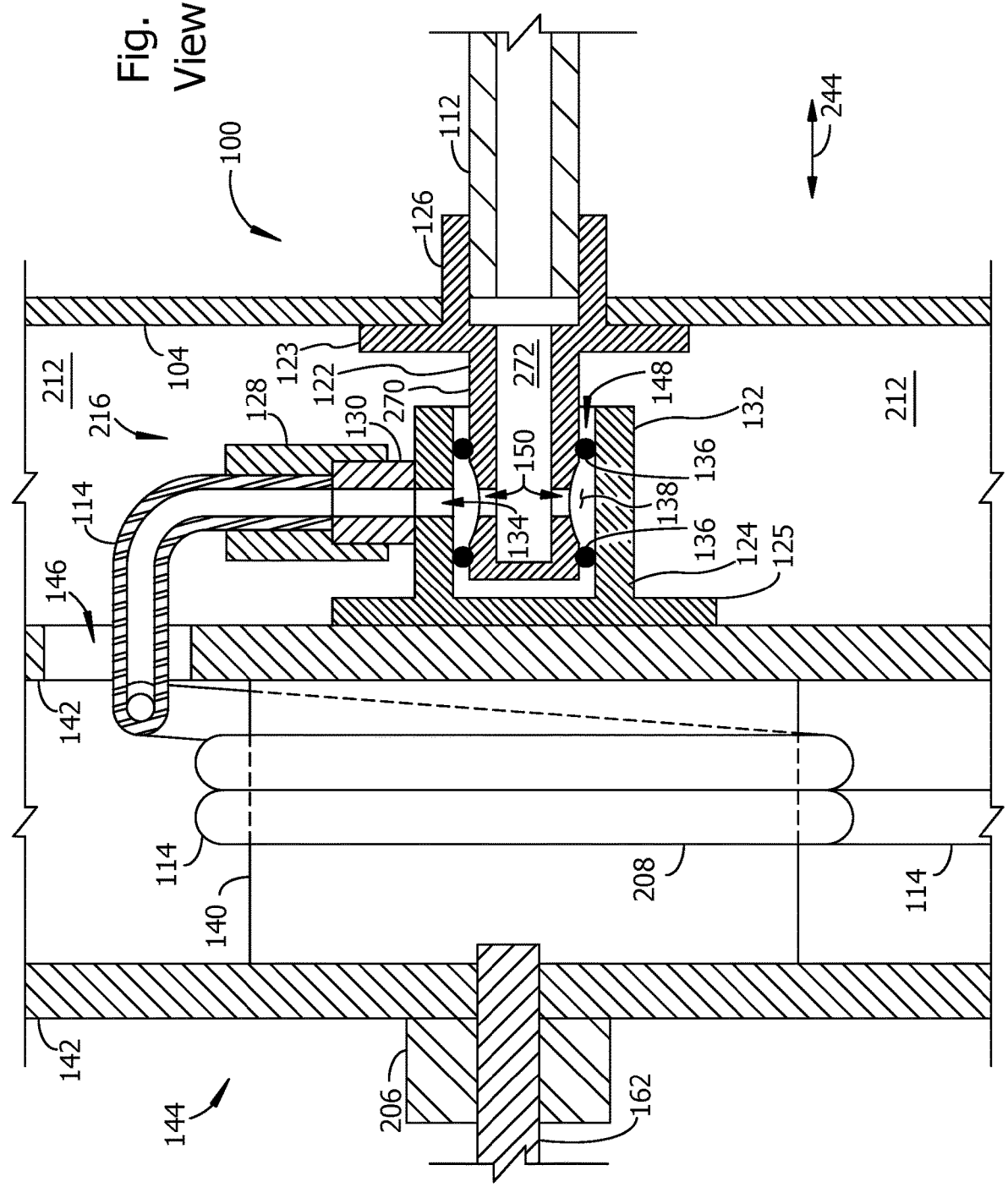
FIG. 5 shows a partial enlarged view A of the example automatic line reel of FIG. 4, illustrating some features of a rotatable reel assembly configured for establishing an uninterrupted fluid flow path between a stationary line and an extendable line wound around the reel assembly.

The reel assembly 144 optionally includes a pair of opposing reel flanges 142 attached to opposite ends of an intervening reel drum 140. In FIG. 4 and FIG. 5, the reel drum 140 has not been cross-sectioned to more clearly show examples of turns of the extendable line 114 wrapping around the reel drum. A rotatable coupling 216 is attached to the opposing reel flange 142. The rotatable coupling 216 prevents the stationary line 112 from twisting or rotating when the reel assembly 144 rotates. In the example reel assembly 144 of FIG. 4 and the example reel assembly 144 of FIG. 5, an end of the extendable line 114 inside the interior space 212 in the covers passes through an extendable line aperture 146 and joins to a hub connector 130 attached to a reel hub 124 of the rotatable coupling 216. An opposite end of the extendable line 114 passes through a second line aperture 120 formed in the base unit 110, the extendable line passing through the interior space 210 in the base unit 110 and out the first line aperture 116.

In embodiments of the reel assembly 144 configured to establish an uninterrupted fluid flow path from the stationary line 112 to the extendable line 114, the rotatable coupling 216 establishes a fluid flow path from the stationary line connector 126 configured for secure attachment of an end 266 of the stationary line 112 to the hub connector 130 configured for secure attachment of the extendable line 114. A fluid such as a gas, liquid, or a mixture of gas, liquid, and/or solid material flows through the rotatable coupling without interruption from rotation of the reel assembly 144 during extension and retraction of the extendable line. The rotatable coupling 216 includes a reel axle 122 and a reel hub 124. In the example reel assembly 144 of FIGS. 4 and 5, the reel hub 124 is attached to a reel flange 142 and/or the reel drum 140, with the reel hub positioned in the void space 212 between the fixed reel cover 106 and the removable reel cover 104. The reel hub 124 optionally includes a hub flange 125 to secure the reel hub 124 to the reel flange and/or reel drum 140. During operation of an embodiment of the automatic line reel 100 to extend or retract flexible line 208, the reel axle 122 and the stationary line 112 remain stationary, i.e. nonrotating, with respect to the base unit 110 and the reel hub 124 rotates with the reel assembly 144 under influence of the motor 160.

The hollow, rigid, stationary reel axle 122 slidably engages the rotatable reel hub 124 through a hub end aperture 148 formed in the reel hub. The reel axle 122 is preferably positioned against the removable reel cover 104 such that the reel hub 124 axis of rotation is coincident with the central axis of rotation of the motor drive shaft, thereby establishing the position of the central axis of rotation 214 for the reel assembly and providing for smooth rotation of the reel assembly about the reel axis under influence of the motor. The reel axle 122 is sufficiently rigid to bear the weight of the reel assembly 144 without substantial flexure, thereby maintaining the integrity of fluid seals established by O-rings 136. For the examples of a reel assembly 144 in FIGS. 4, 5, and 6 the reel axle 122 includes a stationary line connector 126 configured for gas-tight and/or water-tight connection to the stationary line 112 and optionally further includes an axle flange 123 for establishing a strong attachment to the removable reel cover 104. Examples of a stationary line connector include, but are not limited to, a barbed hose fitting, a swaged hose fitting, a threaded hose fitting, and a quarter-turn hose fitting. The hollow interior 272 of the reel axle 122 forms part of the continuous fluid path through the rotatable coupling 216.

Figure 6:
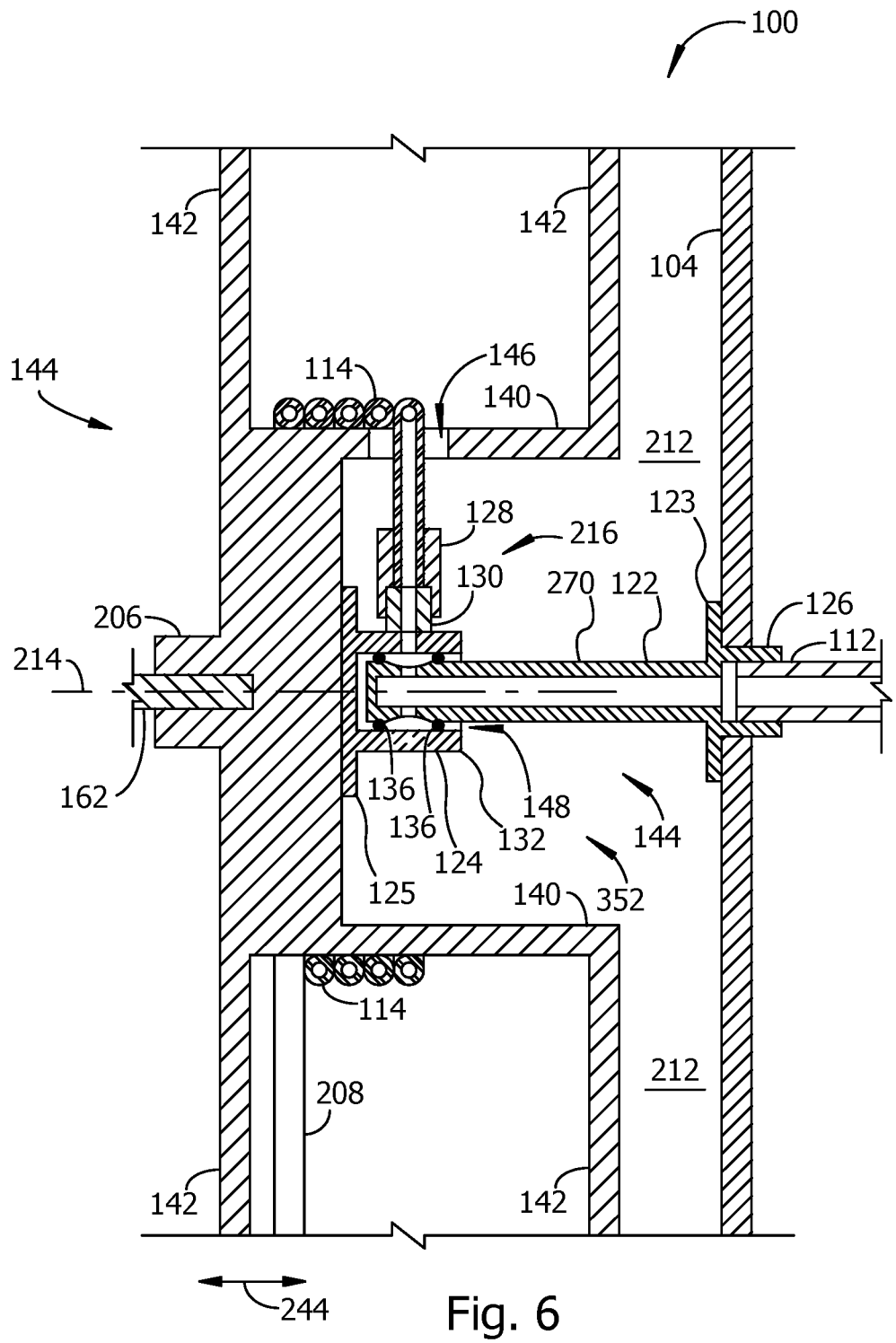
FIG. 6 is an alternative View A showing some details of another example reel assembly.

As shown in the example reel assemblies 144 of FIGS. 4-6, at least one fluid aperture 150 is formed through the outer surface 270 of the reel axle 122 and into the axle void space 272 inside the hollow reel axle. The fluid aperture 150 establishes fluid communication between the stationary line connector 126, the void space 272, and a hub plenum 138 formed between two O-rings 136, the interior sides of the hub end aperture 148, and the outer surface 270 of the reel axle 122 as the reel hub 124 rotates with respect to the reel axle 122. The O-rings are preferably positioned to prevent fluid leakage out of the hub end aperture 148. The hub plenum 138 is in fluid communication with the extendable line 114 through a side wall aperture 134 formed in a hub side wall 132 of the reel hub 124, through the hub connector 130 and through the extendable line connector 128.

In the examples of a reel assembly 144 in FIG. 4 and FIG. 5, the reel hub 124 and other parts of the rotatable coupling 216 are positioned adjacent to and outside the reel drum 140. In the example reel assembly 144 of FIG. 6, the reel hub 140 has an exposed side not covered by a reel flange 142, providing access to a drum void space 352 inside the reel drum. The reel hub 124, hub connector 130, O-rings 136, and optionally other parts of the rotatable coupling 216 are attached to a surface forming a side of the drum void space 352. An extendable line aperture 146 is optionally formed in the sides wall of the reel drum 140 to provide for connection of the extendable line 114 to the hub connector 130 on the reel hub 124.

Figure 7:
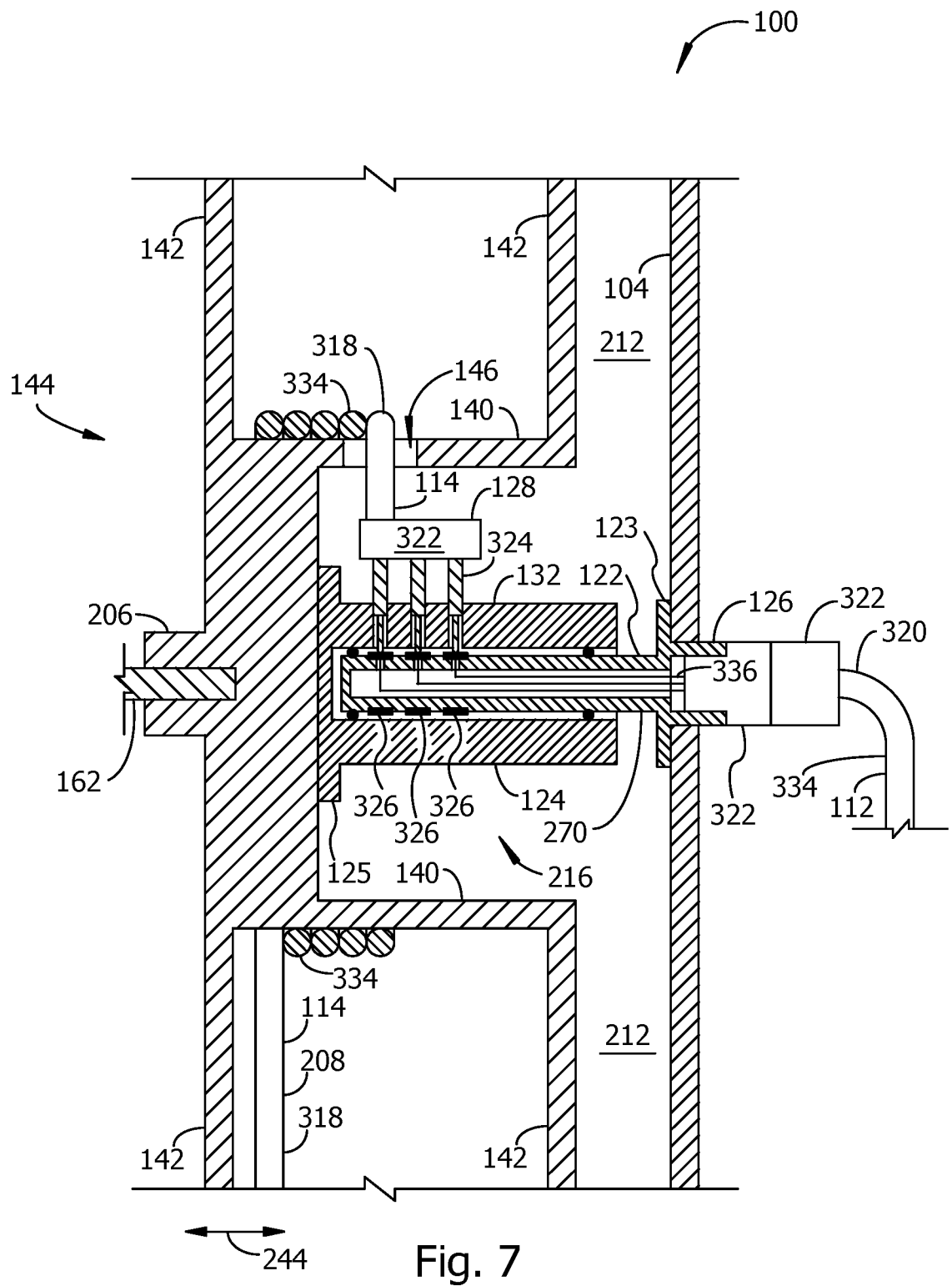
FIG. 7 shows another alternative view A illustrating some features of a rotatable reel assembly configured for establishing uninterrupted electrical connections between a stationary line and an extendable line wound around the reel assembly.

The examples of a reel assembly 144 in FIGS. 4-6 are configured for forming a continuous fluid flow path between the stationary line 112 and the extendable line 114. The continuous flow path is not interrupted by full revolutions of the reel assembly. FIG. 7 shows an example of a reel assembly 144 configured for forming a continuous conduction path for the flow of electrical current from a first electrical cable 334 corresponding to the stationary line 112, through the rotatable coupling 216 and reel assembly, to a second electrical cable 334 corresponding to the extendable line 114. The example reel assembly 144 in FIG. 7 maintains uninterrupted current flow from the stationary line 112 to the extendable line 114 while the reel assembly turns through full revolutions.

As shown in the example of FIG. 7, the reel assembly 144 configured for electrical connections includes the hollow reel axle 122 attached to the removable reel cover 104 and engaged with a rotatable reel hub 124 attached to the reel drum 140, as in other embodiments of the reel assembly. A first electrical connector 322 is attached to an end of the stationary electrical cable 320 and is shown engaged with a corresponding second electrical connector 322 attached to the stationary line connector 126 on the reel axle 122. Electrical conductors 336 pass through the hollow interior of the reel axle 122, with each electrical conductor 336 electrically connected to a separate circumferential electrical conductor 326 on the outer surface 270 of the reel axle 122. A circumferential electrical conductor 326 may be referred to as a slip ring. The spring contact pins are further connected to a third electrical connector 322 electrically connected to conductors in the extendable line 114 wound around the reel drum 140. The spring contact pins 324 and circumferential electrical conductor 326 establish uninterrupted electrical contact between conductors in the stationary electrical cable 334 and corresponding conductors in the extendable electrical cable 318 during full revolutions of the reel hub 124.

During operation of the automatic line reel 100, rotation of the reel assembly 144 is initiated and stopped in response to detections of contact pressure between the extendable line 114 and the triangular pressure transducer 152 positioned inside the base unit 110. Examples of a triangular pressure transducer 152 in accord with the disclosed embodiments of the automatic line reel 100 are shown in FIGS. 8-13, 16-17, and 20-21. An example triangular pressure transducer 152 includes a support frame 218 having three flat transducer side walls 154 joined to one another to form a triangular hollow structure 314 having a transducer void space 248 through which the flexible line 208 passes.

At least one of the transducer side walls 154 has a flat interior surface 274 to which is attached a first 176 flat pressure sensor 158. A triangular pressure transducer optionally includes a second 178 flat pressure sensor 158 to another of the three transducer side walls 154. A third 180 flat pressure sensor 158 is optionally attached to the third of the three transducer side walls 154. The triangular hollow structure 314 requires fewer flat pressure sensors 158 to reliably detect contact with a flexible line 208 than hollow structures formed with more than three interior surfaces, whether the automatic line reel is used while resting on a horizontal surface such as a floor or tabletop or while attached to a vertical surface such as a wall. Experimentation has shown that a pressure transducer with pressure sensors on a support frame having more than three side walls does not improve detection of contact pressure from the extendable line 114 compared to the disclosed embodiments with a support frame having no more than three side walls. The outer edges of the transducer side walls 154 may be chamfered or rounded as suggest at a chamfered corner 316 in FIG. 10.

Figure 9:
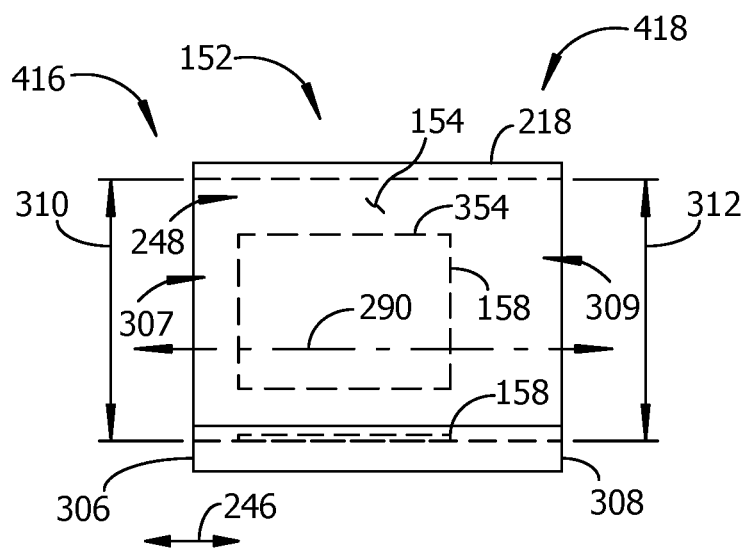
FIG. 9 is a side view of the example triangular pressure transducer of FIG. 8.

As suggested in the example of FIG. 9, each flat pressure sensor 158 has an approximately rectangular outer perimeter shape, although sensors with other perimeter shapes may optionally be used. Each pressure sensor 158 is preferably attached to the support frame 218 with a longest edge 354 of the sensor approximately parallel to the longitudinal axis 290 of the triangular pressure transducer 152.

Each of first pressure sensor 176, the optional second pressure sensor 178, and the optional third pressure sensor 180 in the triangular pressure transducer 152 is a flat pressure sensor 158 having a variable impedance which changes in response to pressure applied to the sensor, for example a contact pressure resulting from the extendable line 114 pressing against the pressure sensor 158. Each pressure sensor 158 is preferably attached to a relatively flat surface for optimum performance of the sensor. The interior surfaces 274 of the each of the transducer side walls 154 of the triangular pressure transducer are therefore flat, in contrast for example to the curved interior surface of a hollow cylinder. Furthermore, each flat pressure sensor is positioned entirely on one flat interior surface and does not extend on to an adjacent surface nor over an intersection of two adjacent surfaces. As shown in the example of FIG. 10, each flat pressure sensor 158 preferably has a width dimension 294 that is in a range from 60% to 90% of a width dimension 292 of the interior flat surface 274 to which the sensor is attached.

Figure 11:
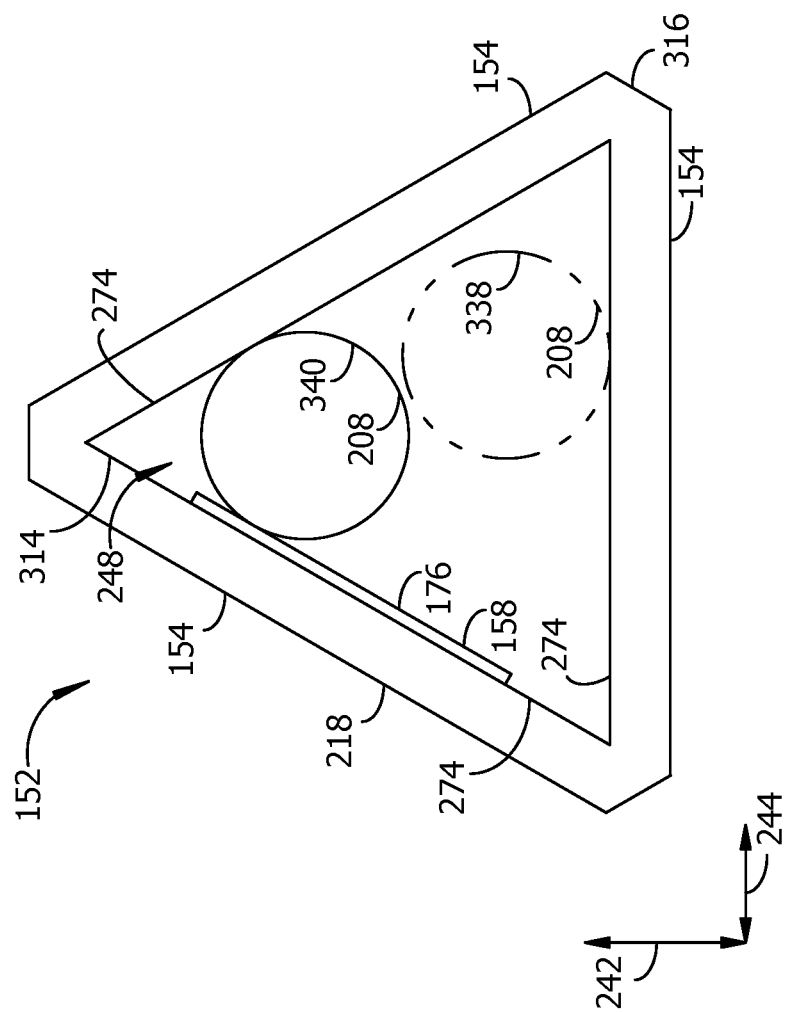
FIG. 11 is an end view of an example embodiment of the triangular pressure transducer with a maximum of one pressure sensor and an example of an extendable line in position to activate the pressure sensor.

FIG. 11 illustrates an example of the triangular pressure transducer 152 having a maximum of one pressure sensor 158. FIG. 11 further illustrates two example positions of a flexible line 208 passing through the transducer void space 248. A first example position 338 shows the flexible line in contact with an interior surface of the support frame 281 but not in contact with the flat pressure sensor 158. A second example position 340 of the flexible line 208 shows the line displaced upwards in a vertical direction 242 and in a transverse direction 244 from the first position 338.

As the flexible line 208 is pulled upwards, for example by a person connected to the flexible line moving away from the automatic line reel 100 or by the person gripping the line and pulling it away from the automatic line reel, the flexible line will be urged into firm contact with the pressure sensor 158 at the second position 340 by sliding contact with the interior surfaces 274 of the triangular hollow structure 314. Should the contact pressure exceed a first pressure threshold 202 stored in the automatic line reel 100, the processor in the automatic line reel starts rotation of the reel assembly to extend the flexible line 208. The processor may be configured to stop rotation of the reel assembly and extension of the flexible line from the automatic line reel when contact pressure between the flexible line and the pressure sensor falls below a second pressure threshold 203 stored in the automatic line reel. Reel rotation is optionally continued for a preset time interval after contact pressure decreases below the second threshold to extend a small amount of slack in the flexible line 208. After rotation of the reel assembly stops, the flexible line may fall to the first example position 338 (i.e., no pressure sensor contact) or may slide along the pressure sensor, possibly maintaining contact with the sensor but not pressing against the sensor firmly enough to exceed the first pressure threshold.

Examples of a processor suitable for use in the disclosed embodiments include, but are not limited to, a microprocessor implemented in semiconductor hardware, a microcontroller implemented in semiconductor hardware, a central processing unit (CPU) forming part of a microprocessor or microcontroller implemented in a programmable logic device, and a CPU, microprocessor, or microcontroller implemented in a gate array.

As suggested in the example of FIG. 11, an automatic line reel having a triangular pressure transducer 152 with no more than one pressure sensor 158 is effective for removing slack line when the direction of pull on the flexible line has a substantial component in the vertical direction 242. However, in some circumstances the direction of pull on the flexible line may have a direction of pull with a substantial component in a transverse direction 244 relative to the longitudinal axis 290 of the triangular pressure transducer 152, and a vertical component that is insufficient to displace the flexible line substantially upwards to the second position 340. Such a situation may occur, for example, when a person is connected to the automatic line reel 100 by a very long flexible line 208, possibly with much of the line resting on the floor, or when the line has been pulled around a table leg or door frame as the person moves away from the apparatus.

Figure 12:
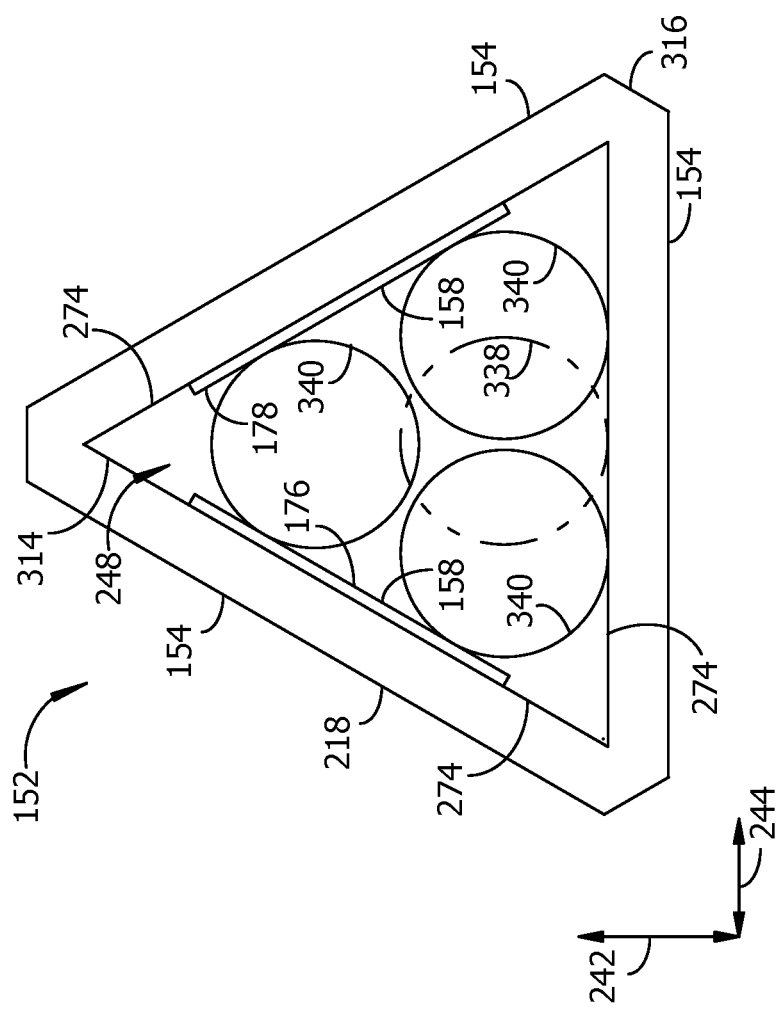
FIG. 12 is an end view of another embodiment of the triangular pressure transducer with a maximum of two pressure sensors, showing examples of positions of the extendable line for activating each pressure sensor individually and for activating both pressure sensors simultaneously.

A triangular pressure transducer 152 will reliably sense contact pressure for a pull on the flexible line having a substantial component in a transverse direction 244 toward either longitudinal side of the automatic line reel when a second flat pressure sensor 158 is included in the triangular pressure transducer. An example of a triangular pressure transducer with a first pressure sensor 176 on an interior flat surface 274 and a second pressure sensor 178 on an adjacent flat surface 274 is shown in FIG. 12. As suggested in the example of FIG. 12, a pull on the flexible line may displace the line from a first position 338 in a vertical direction 242 until the flexible line establishes contact with both the first 176 and second 178 pressure sensors. When the pull is in a substantially transverse direction 244, the flexible line may be displaced into contact with the first pressure sensor 176 and the bottom surface of the triangular hollow structure 314, where no pressure sensor 158 is installed. When the pull is in an opposite transverse direction, the flexible line may be displaced into contact with the second pressure sensor 178 and the bottom surface. Should the pressure against either the first or second pressure sensors exceed the first pressure threshold, rotation of the reel assembly will be initiated by the processor. The triangular pressure transducer in the example of FIG. 12 is therefore effective for starting and stopping line extension from an automatic line reel 100 placed on a low horizontal surface, particularly when a sufficiently long flexible line 208 has been stored on the reel assembly that a person attached to the line may walk around furniture or walk from one room to another before line extension is initiated by a pull on the line.

When the automatic line reel is positioned on an elevated horizontal surface such as a table top or when the automatic line reel is attached to a vertical surface such as a wall in a room or the side of an equipment trolley, a pull on the flexible line could displace the flexible line in almost any direction inside the triangular pressure transducer 152, forcing the line into contact with any one of the pressure sensors 158, and sometimes in simultaneous contact with two pressure sensors 158. A third pressure sensor 180 is optionally included in some embodiments of the triangular pressure transducer 152 to provide for detection of contact pressure from a flexible line pulled from almost any direction. For example, the flexible line may start from an initial position 338 not in contact with any pressure sensor 158. A displacement in a transverse direction 244 may bring the flexible line into a position 340 with sufficient contact pressure against the first pressure sensor 176 to activate line extension. A displacement in an opposite lateral direction may bring the flexible line into contact with the second pressure sensor 178 to activate line extension. Likewise, a displacement establishing contact with the third pressure 180 may activate line extension.

Figure 13:
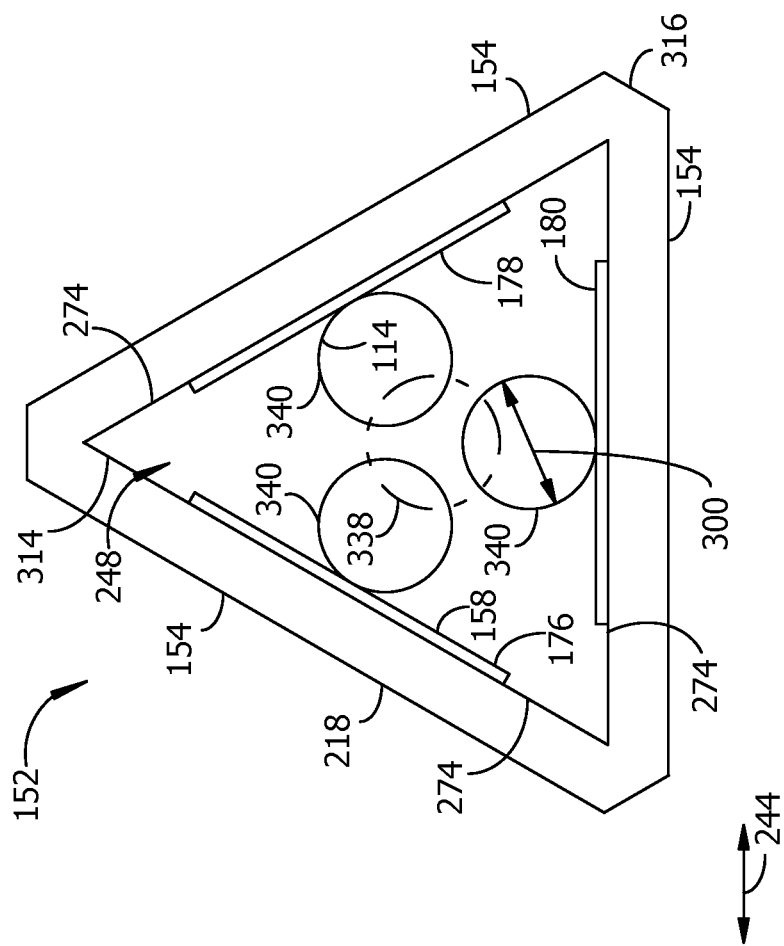
FIG. 13 is an end view of the example triangular pressure transducer of FIG. 9, showing examples of the extendable line in different positions for activating an example triangular pressure transducer with three pressure sensors.

The automatic line reel 100 may be configured to initiate line extension when only one pressure sensor has been contacted by the flexible line as suggested in FIG. 13 or alternatively when two pressure sensors have been contacted as in FIG. 12. A diameter 300 of the flexible line may be used to determine whether contact with one pressure sensor or two pressure sensors is sufficient to initiate and stop rotation of the reel assembly.

FIGS. 8-13 illustrate an advantage of a support frame 218 consisting of three flat sides over other pressure sensor support structures having more than three sides. In the example of FIG. 11, a displacement in a vertical direction 242 brings the flexible line into contact with the first pressure sensor 176, which in the example of FIG. 11 is the only pressure sensor 158 installed in the triangular pressure transducer. As the flexible line moves upward and comes into contact with the pressure sensor, a contact force between the flexible line and the pressure sensor will have a substantial component normal to the surface of the pressure sensor resulting from the angle of the interior surface 274 relative to the vertical displacement direction 242. The response of the automatic line reel 100 is readily calibrated to measure the normal component of the contact force and compare the normal component of the contact force to the relevant activation pressure threshold. However, should the support frame have four sides instead of three, two of the sides may be positioned at a small angle to the vertical displacement direction 242. A displacement of the flexible line in a vertical direction may cause the flexible line to slide along the vertical surface of a pressure sensor attached to one of the vertical interior walls of the four-sided frame, without producing sufficient contact force in a direction normal to the sensor surface to activate the sensor. A four-sided transducer may therefore need more pressure sensors and/or greater contact forces to reliably detect contact pressure than a three-sided pressure transducer.

Figure 14:
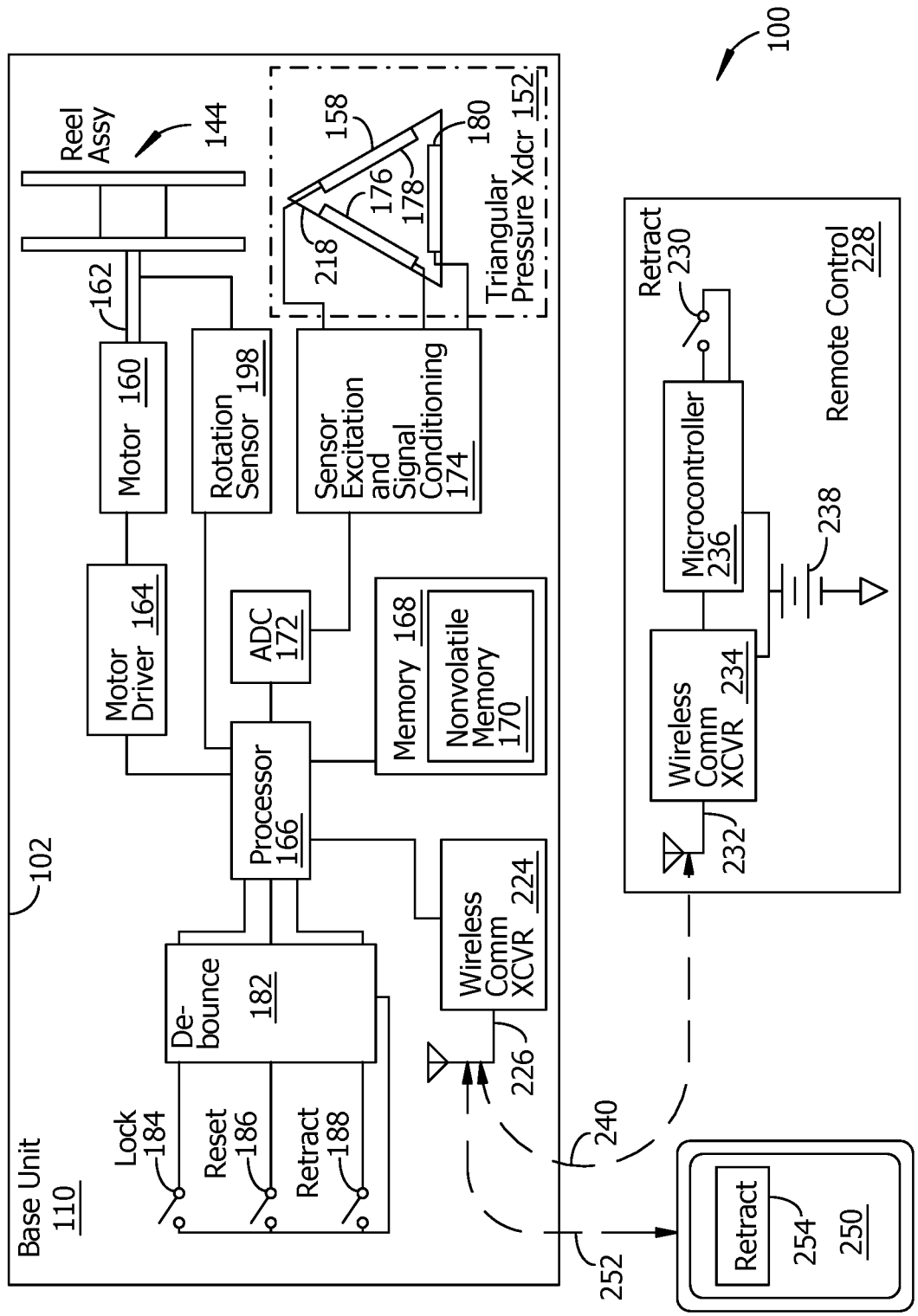
FIG. 14 is a schematic diagram showing examples of components and electrical connections included in embodiments of the automatic line reel.

FIG. 14 is a schematic diagram showing examples of electrical components and electrical connections for detecting pressure signals from the triangular pressure transducer 152 and controlling the extension and retraction of the extendable line 114 in response to detected signals and command inputs. As suggested in the example of FIG. 9, a first pressure sensor 176, an optional second pressure sensor 178, and an optional third pressure sensor 180 in the triangular pressure transducer 152 are electrically connected to a sensor excitation and signal conditioning circuit 174. An analog-to-digital converter (ADC) 172 converts electrical signals from each pressure sensor into digital values sent to the processor 166. The processor 166 receives the digital values and outputs control signals to the motor 160 through a motor driver 164, for example to initiate motor rotation, set a motor rotation speed and direction, and to stop motor rotation. In some embodiments 100, the processor 166 receives a signal from a rotation sensor 198 configured to output a count pulse for each rotation of the motor drive shaft 162. In some embodiments 100, the processor may determine the length of flexible line extended out of the reel assembly and the amount of flexible line remaining on the reel assembly by keeping track of a total number of count pulses received as the extendable line 114 is extended or retracted by the motor 160 under command of the processor 166. In some embodiments 100, the processor 166 is configured to stop extension of the extendable line 114 when a pulse count indicates that a predetermined portion of the total length of line available for extension has been unwound from the reel assembly 144.

Electrical switches attached to the outer enclosure 102 and electrically connected to the processor 166 through an optional switch debounce circuit 182 may be activated to control calibration and operation of the automatic line reel 100. Examples of command switches include, but are not limited to, a lock switch 184 to prevent accidental activation of the motor 160, a reset switch 186 to return the processor to a known initialization state and optionally to record a pulse count total corresponding to a fully extendable line 114, for example after line replacement, and a retract switch 188 to initiate rotation of the reel assembly in a direction to retract the extendable line and wind the line onto the reel assembly.

A wireless remote control 228 optionally included with an embodiment 100 is configured to enable a person using the apparatus to command retraction of the extendable line 114 without returning to the base unit 110. In an embodiment 100 with a wireless remote control 228, the processor 166 in the base unit 110 is connected for signal communication with a wireless communications transceiver 224. The wireless communications transceiver 224 sends and receives data through an antenna 226 in the base unit 110. Another antenna 232 and another wireless communications transceiver 234 in the wireless remote control 228 carry data and commands to and from a microcontroller 236 in the remote control 228. The microcontroller 236 and wireless communications transceiver 234 in the remote control 228 receive electrical power from a battery 238 in the remote control. The communications transceiver 234 in the remote control 228 is configured to establish a wireless data communication link 240 with the communications transceiver 224 in the base unit 110. When the microcontroller 236 detects activation of a retract switch 230 on the remote control 228, the microcontroller communicates the switch activation to the processor 166 in the base unit 110, thereby requesting the processor 166 initiate retraction of the flexible line.

The retract switch 230 on the remote control 228 is preferably operable by a person with impaired manual dexterity. Examples of the retract switch 230 include, but are not limited to, a toggle switch, a pushbutton switch, a pressure sensor, a switch activated by a squeeze bulb, a switch activated by a puff of air, a switch activated by eye movement, a sound-activated switch, a touchpad, a photoelectric switch, and a proximity switch.

Figure 15:
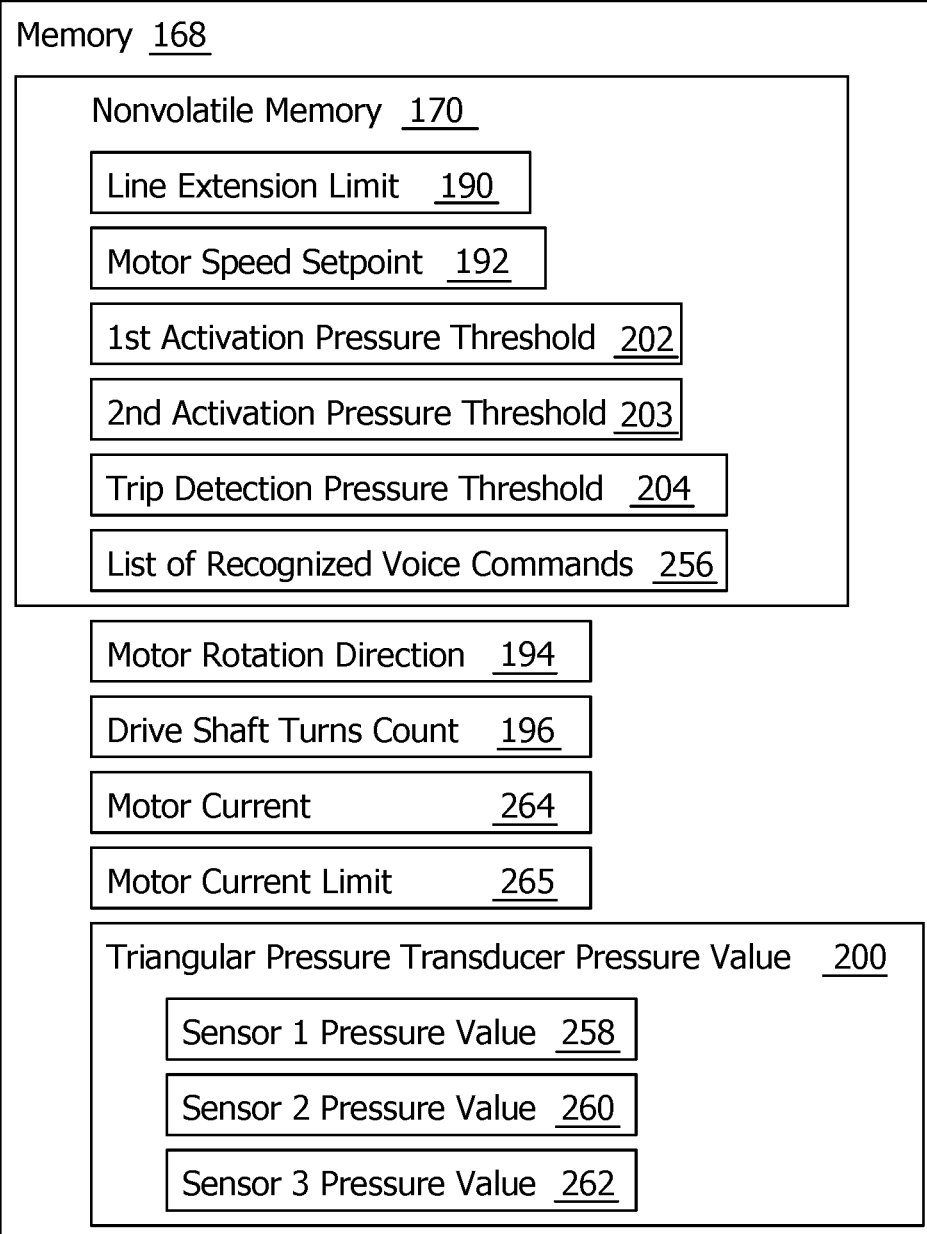
FIG. 15 is a block diagram of optional parameters stored in volatile and/or nonvolatile memory included in embodiments of the automatic line reel.

The processor 166 is configured to determine and/or control operating and safety parameters for the automatic line reel 100. Examples of parameters accessible to the processor 166 are shown in FIG. 15. Some parameters, for example a pulse count value corresponding to a line extension limit 190 for the extendable line 114, a motor rotational speed setpoint value 192, and one or more pressure thresholds are optionally stored in a nonvolatile memory 170. A first activation pressure threshold 202 optionally corresponds to a value of contact pressure between the flexible line 208 and the triangular pressure transducer 152 that causes the processor to activate rotation of the reel assembly 144 and extend the flexible line 208 from the base unit 110. A second activation pressure threshold 203 optionally corresponds to a value of contact pressure that causes the processor to stop rotation of the reel assembly. A third activation threshold pressure threshold 204 represents a value of contact pressure corresponding to a person stumbling against the extendable line and therefore represents a trip detection pressure threshold. The first 202, second 203, and third 204 activation pressure thresholds optionally have large enough values that the weight of the line is not sufficient to exceed one of the activation thresholds.

The processor optionally measures a time duration over which contact pressure detected by a pressure sensor increases from a static value to a peak value to make an estimate that a person may be in the act of tripping over the extendable line 114. The processor may respond to a detection at the third activation pressure threshold 204 by rapidly unwinding the extendable line 114 from the reel assembly or by allowing the reel assembly to spin freely to help prevent the person tripping on a line under tension.

Other measured values and operating parameters may optionally be stored in a volatile memory 168 each time the apparatus is activated. Examples of operating parameters include a motor rotation direction 194, a count of drive shaft turns 196 from the rotation sensor 198, a measured value of motor current 264, a value for a motor current limit 265, and measured values of impedance from which the processor 166 determines a triangular pressure transducer pressure value 200. The optional motor current limit 265 represents, for example, a current value corresponding to a stalled motor or an overheating motor. The triangular pressure transducer pressure value 200 may be calculated by the processor 166 from a sensor 1 pressure value 258 measured from the first pressure sensor 176, a sensor 2 pressure value 260 measured from the optional second pressure sensor 178, and a sensor 3 pressure value 262 measured from the optional third pressure sensor 180 in the triangular pressure transducer 152.

An automatic line reel 100 is optionally configured to prevent over-extension and/or over-retraction of the extendable line 114. Over-extension may cause the extendable line to detach from the reel assembly. Over-retraction may cause the extendable line to pull against the person to whom the line is attached or place sufficient tension on the line to damage the line or line connections. Some embodiments of the automatic line reel 100 count revolutions of the drive shaft and/or reel assembly, comparing the count to the stored value of the line extension limit 190 and halting rotation of the reel assembly when the count exceeds the line extension limit. An automatic line reel optionally includes a line stop, and optionally two line stops, attached to the extendable line 114 to halt rotation of the motor when a line stop contacts a flat pressure sensor 158 in the triangular pressure transducer 152. One of the two optional line stops is positioned to prevent over-retraction. The second optional line stop, when provided, is positioned to prevent over-extension of the extendable line. The processor 166 and/or the microcontroller 236 are optionally configured to halt motor rotation when over-retraction has been detected, overriding activation of the retract switch 230 and/or a retract command from applications software 254 on a smart phone 250 to prevent further increases in tension in the extendable line. The processor 166 optionally responds to a detection of over-retraction by overriding activation of the retract switch and unwinding a preset length of extendable line from the reel assembly 144. The processor optionally responds to a detection of over-extension by quickly halting motor rotation.

Figure 16:
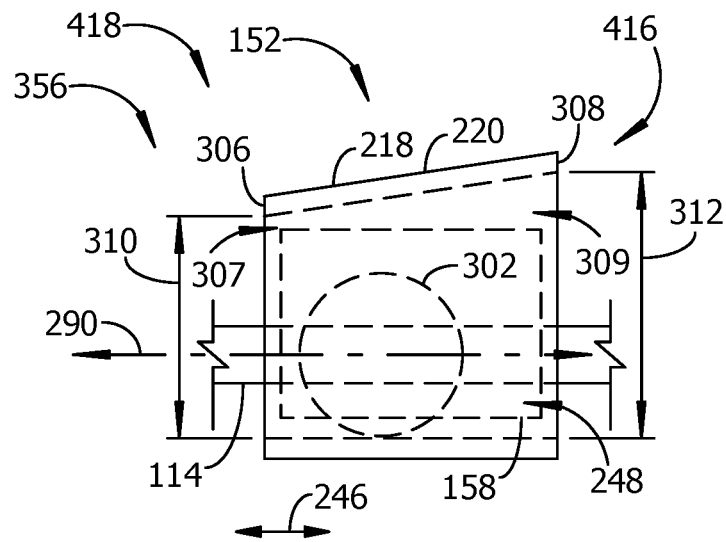
FIG. 16 is a side view of another example support frame for a triangular pressure transducer, and further illustrating an example of a line stop affixed to the extendable line with the line stop in an example position for activating a pressure sensor.
Figure 17:
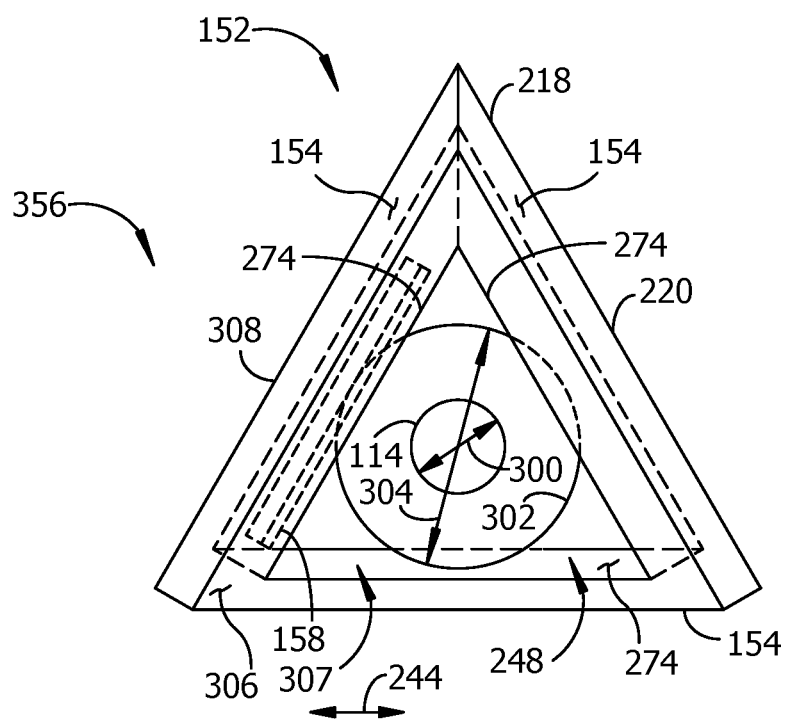
FIG. 17 is an end view of the example support frame, extendable line, and line stop of FIG. 16, further illustrating an example of the line stop positioned in a void space inside the support frame, with the line stop too large to pass through an aperture at an end of the support frame but small enough to pass through an aperture at the opposite end of the support frame.
Figure 18:
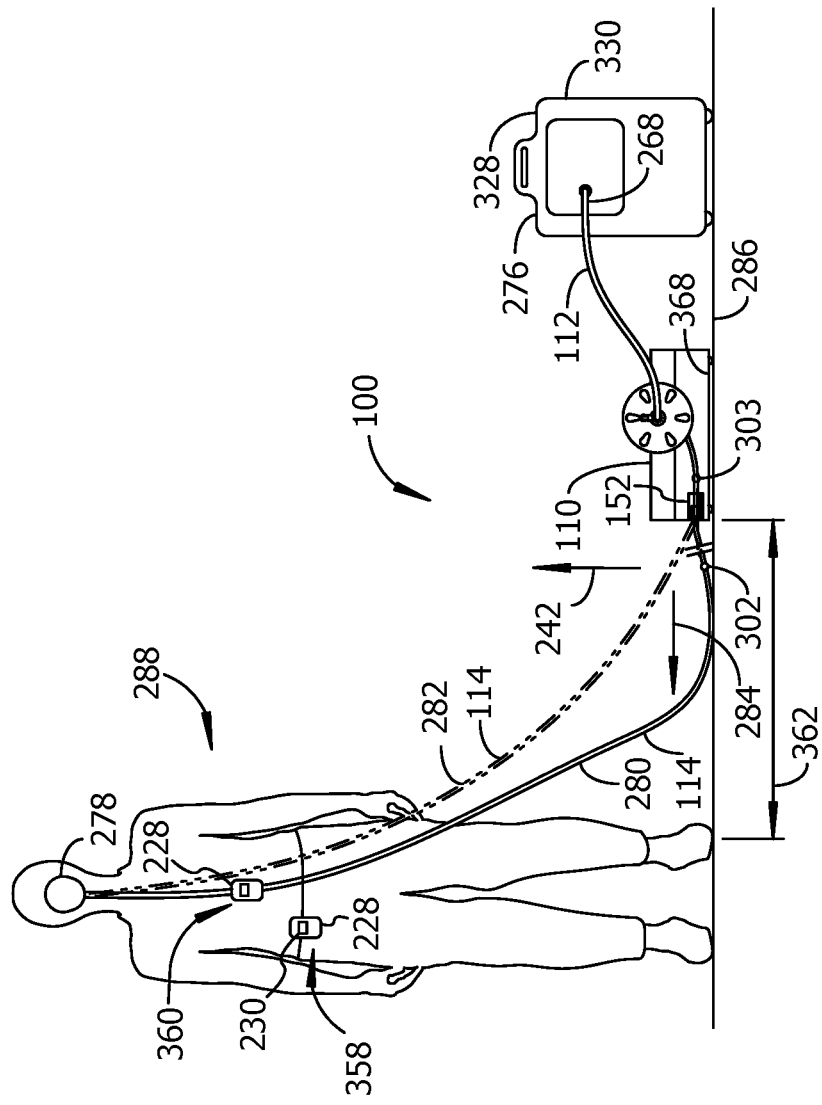
FIG. 18 illustrates an example of a person using an embodiment of the automatic line reel with examples of the automatic line reel, an oxygen supply, and a fluid collection vessel or monitoring instrument resting on a floor.

FIGS. 16-18 show examples of a first optional line stop 302 and a second optional line stop 303 attached to the extendable line 114. The line stop(s) reduce an amount of transverse and/or vertical displacement of the extendable line needed to activate a pressure sensor 158 and modify rotation of the reel assembly 144. A diameter 304 of the line stop 302 is substantially larger than the outer diameter 300 of the extendable line, as shown in the example of FIG. 17. The line stop diameter 304 is optionally selected to cause the line stop to fit into the transducer void space 248 with a sliding fit against the interior flat surfaces 274 of the triangular pressure transducer. As the extendable line 114 pulls the line stop 302 across the interior surfaces 274, the line stop 302 presses against the flat pressure sensor(s) 158, each pressure sensor extending outward from the interior flat surfaces 274. When the line stop applies sufficient pressure against a pressure sensor to exceed the second activation pressure threshold 203, the processor 166 detects activation of the triangular pressure transducer and stops rotation of the reel assembly 144.

Figure 8:
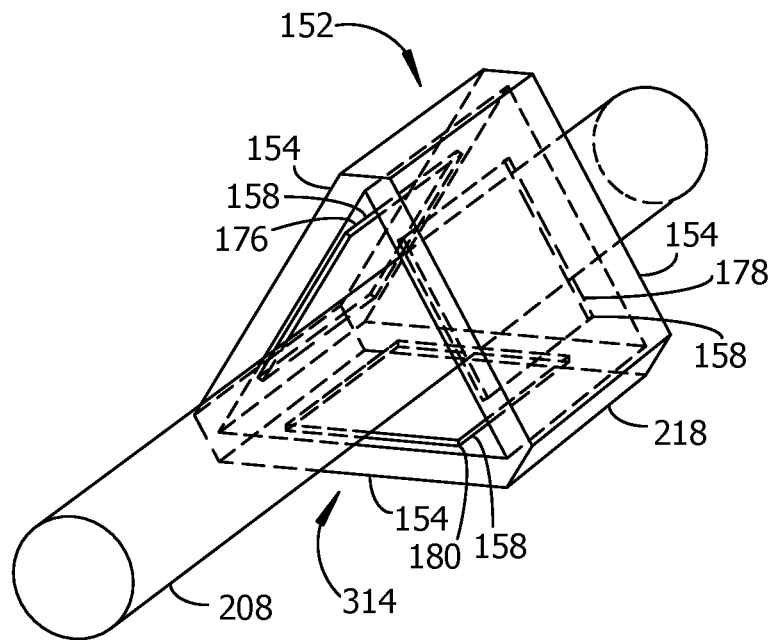
FIG. 8 is a pictorial view of an example triangular pressure transducer included in some embodiments of the automatic line reel.

The interior height 310 of the transducer void space 248 at a first end 306 of the triangular pressure transducer 152 and the interior height 312 of the transducer void space 248 at a second end 308 of the triangular pressure transducer 152 are approximately equal to one another in the examples of FIG. 8 and FIG. 9. The line stop 302 may therefore pass all the way through the transducer void space 248, for example passing completely through an aperture 307 at the first end 306, through the transducer void space, and completely through an aperture 309 at the second end 308 as the line stop moves with extension or retraction of the extendable line 114.

In some embodiments of the support frame 218, the transducer side walls 154 are shaped to give the support frame 218 a tapered profile, causing a separation distance between opposite side walls to increase from a height dimension 310 at the first end 306 to a larger height dimension 312 at the second end 308 opposite the first end, as shown in the examples of FIG. 16 and FIG. 17. When placed in an enclosure with a reel assembly, the first end 306 is the outboard end 418 and the second end 308 is the inboard end 416. The outer diameter 304 of the line stop 302 is optionally selected to enable the line stop to pass through the aperture 309 at the second end 308 of the tapered support frame 220 and into the transducer void space 248 sufficiently far to activate a flat pressure sensor 158. For the tapered support frame 220, the outer diameter 304 of the line stop 302 may further be selected to prevent the line stop from passing entirely through the aperture 307 at the first end 306 and fully exiting the transducer void space 248, as suggested in the example of FIG. 17. A tapered triangular pressure transducer 356 requires no more than one flat pressure sensor 158 attached to an interior flat surface 274 of the support frame 218 to accurately detect contact of the line stop and pressure sensor for all directions of pull on the extendable line 114 expected for operation of the automatic line reel 100, for both horizontal and vertical installations of the automatic line reel.

Figure 19:
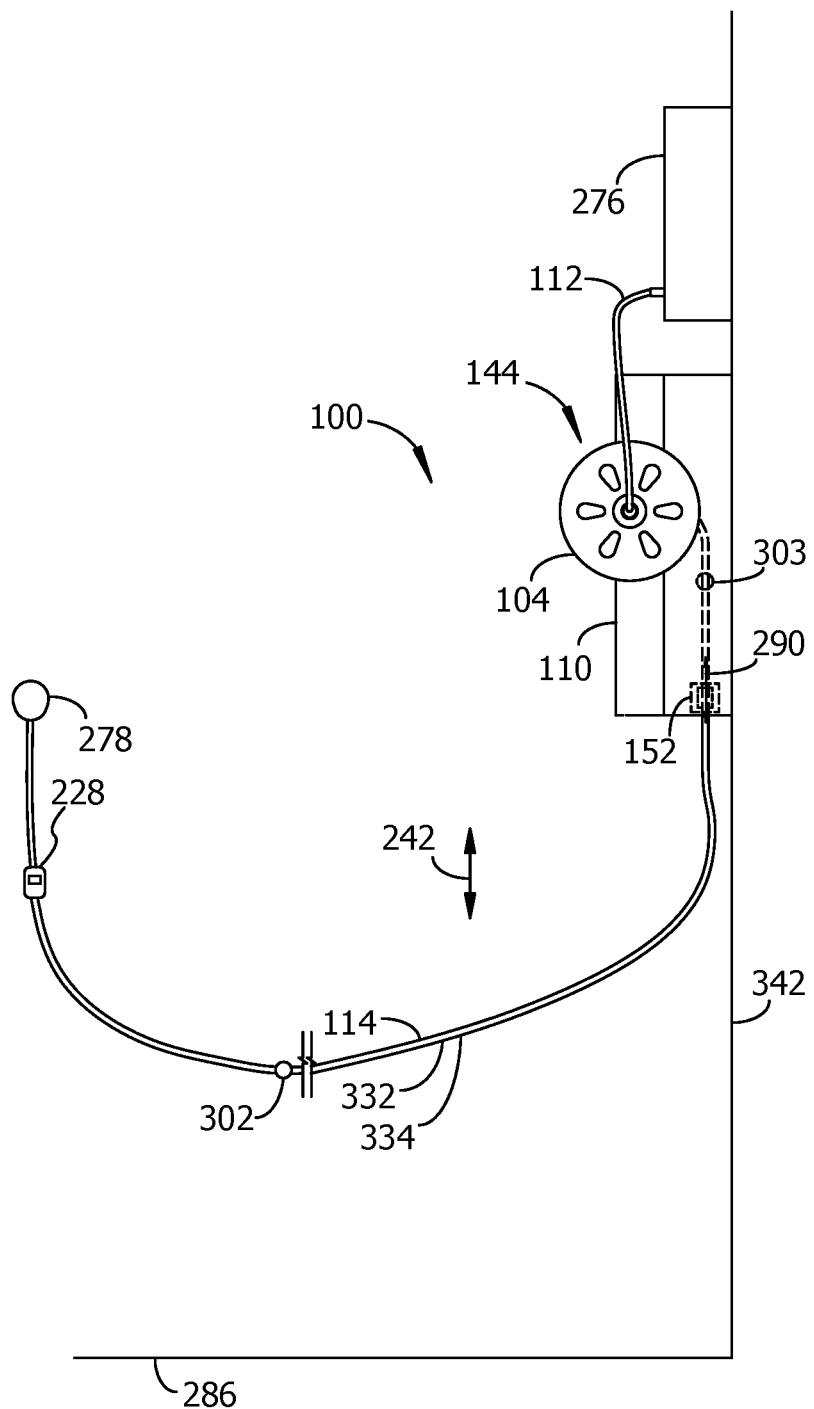
FIG. 19 illustrates an example of the automatic line reel attached to a vertical surface such as a wall.

FIG. 18 and FIG. 19 show examples of an automatic line reel 100 positioned to manage slack in a flexible line. In the example of FIG. 18, the automatic line reel 100 is resting on a horizontal surface 286, for example the floor of a room. When resting on a horizontal surface, the longitudinal axis 290 of the triangular pressure transducer in the automatic line reel is approximately parallel to the horizontal surface. The extendable line 114 is coupled in the example figure to an oxygen mask 278 worn by a person 288. The extendable line 114 preferably has a small amount of slack, represented in FIG. 18 by an example slack line 280 with no kinks, loops, tangles, or line accumulated in a pile on the floor. An end 268 of the stationary line 112 connects an oxygen supply 276 to the automatic line reel 100.

The slack line 280 places less tension on the oxygen mask 278 than a line pulled taught enough to activate the triangular pressure transducer, for example the extendable line 114 shaped into a catenary curve 282 by tension in the line and the weight of the line. The catenary curve 282 represents an extendable line with essentially no slack. As the person moves in a direction away 284 from the automatic line reel 100, slack in the line 280 is removed, a separation distance 362 between the person and the base unit 110 increases, tension in the line increases, and the line is displaced in a vertical direction 242. With sufficient vertical displacement and tension in the extendable line 114, the line under tension 282 presses against a pressure sensor in the triangular pressure transducer 152 with sufficient force to exceed the first activation pressure threshold 202, leading to extension of more flexible line from the automatic line reel 100 until the line again has a small amount of slack 280.

When the person 288 moves closer to the automatic line reel, slack may accumulate in the extendable line 114. Excessive slack presents a potential tripping hazard to the person. The person may therefore remove slack in the line by activating the retract switch 230 on the remote control 228, by pressing a touch target displayed by applications software 254 on a smart phone 250, or by speaking a command recognized by the applications software 254. The applications software 254 may compare words spoken by the person to a list of recognized voice commands 256 stored in memory in the smart phone and/or memory 170 accessible to the processor 166. The applications software 254 is configured to establish a wireless data communications link 252 with the wireless communications transceiver 224 connected to the processor 166.

The wireless remote control 228 optionally includes a clip or clamp (not shown) enabling the remote control to attach to an article of clothing. An example remote control 358 including a clip or clamp configured to attach the remote control to a belt, waistband, or pocket is shown in FIG. 18. The clip or clamp may optionally be configured to attach the remote control to the extendable line 114. FIG. 18 further illustrates an example remote control 360 attached to the extendable line. As suggested in the example of FIG. 18, more than one remote control 228 may optionally be provided with an automatic line reel 100. A remote control 228 may be carried and/or operated by a person other than the person to whom the extendable line 114 is attached, for example a caregiver or personal assistant.

In the example of FIG. 18, a person 288 receives oxygen in an uninterrupted flow path from the oxygen supply through the stationary line 112, automatic line reel 100 and extendable line 114. The extendable line may alternatively be configured for connection to a surgical drain site or an intravenous fluid port on the person, or may be replaced with an electrical cable for carrying electrical signals. The oxygen supply may be replaced with a monitoring instrument 328 or a fluid storage vessel 330. The automatic line reel 100 is advantageous for limiting an amount of slack in the extendable line 114 whether the line is configured for fluid transmission, for example a hose 332, or the transmission of electrical signals in an electrical cable 334.

FIG. 18 further illustrates examples of an extendable line having a line stop 302 positioned to halt rotation of the motor 160 when the line stop contacts a flat pressure sensor 158 in the triangular pressure transducer 152. As suggested in FIG. 18, the line stop is optionally attached to the extendable line 114 to halt motor rotation before the extendable line retracts into the automatic line reel 100 far enough to pull uncomfortably against the person 288. To prevent over-retraction, the line stop 302 may be positioned about two to three meters from the end of the extendable line attached to the person. A second optional line stop 303 may be attached to the extendable line between the triangular pressure transducer 152 and the end of the extendable line attached to the reel assembly 144. The optional second line stop 303 stops rotation of the motor 160 before the extendable line is fully unwound from, and possibly detached from, the reel assembly 144. An automatic line reel 100 optionally includes only the first line stop as at 302 in FIG. 18, only the second line stop as at 303 in FIG. 18, both lines stops, or no line stops.

The optional tapered support frame 218 may be positioned with the first end 306 and the smaller height dimension 310 closest to the line aperture 116 and the line stop positioned as in the example of the line stop 303 in FIG. 18. With this arrangement, the line stop prevents over-extension of the extendable line and possible separation of the line from the reel assembly. Alternately, the tapered support frame may be positioned with the second end 308 and the larger height dimension 312 closest to the line aperture 116 and the line stop positioned as in the example of the line stop 302 in FIG. 18 to prevent over-retraction of the extendable line. The examples of a first optional line stop 302 and a second optional line stop 303 in FIG. 18 and FIG. 19 are optionally used with the examples of a triangular pressure transducer 152 in FIG. 9 and a tapered triangular pressure transducer 356 in FIG. 16.

The processor 166 is optionally configured to measure a magnitude of electrical current 264 drawn by the motor 160 and compare the measured electrical current 265 against a value for a motor current limit 265 stored in memory 168, where the motor current limit 265 optionally corresponds to a stalled motor. A processor configured to measure motor current 264 preferably halts rotation of the motor when a stall is detected. A stall may be caused by a line stop pressing against the support frame 218 or part of the outer enclosure 102 or base unit 110. A stall may be caused by, for example, a person depressing the retract command switch 230 after the extendable line is fully retracted, by the extendable line becoming trapped against a chair leg or under a carpet, or by a person sitting or stepping on the extendable line. Alternately, the processor may be configured to detect a stall by determining that count pulses are not being received from the motor rotation sensor 198 while the retract command switch 230 is activated.

FIG. 19 illustrates an example of the automatic line reel 100 attached to a vertical surface 342 such as a wall or an equipment rack. The longitudinal axis 290 of the triangular pressure transducer 152 is approximately parallel to the vertical surface 342 in the example figure. The oxygen supply 276 is attached to the vertical surface above the automatic line reel 100 but may alternatively be positioned to one side or below the automatic line reel.

The examples of a triangular pressure sensor 152 shown in FIGS. 8-14 and 16-17 each optionally have three flat pressure sensors 158, one sensor on each of three transducer side walls 154 joined to one another to form a hollow triangular structure 314. A first pressure sensor 176 may be attached to an interior flat surface 274 of a first transducer side wall 155, a second pressure sensor 178 may be attached to an interior flat surface 274 of a second transducer side wall 156, and a third pressure sensor 180 may be attached to an interior flat surface 274 of a third transducer side wall 157, as suggested in the example of FIG. 10.

Figure 20:
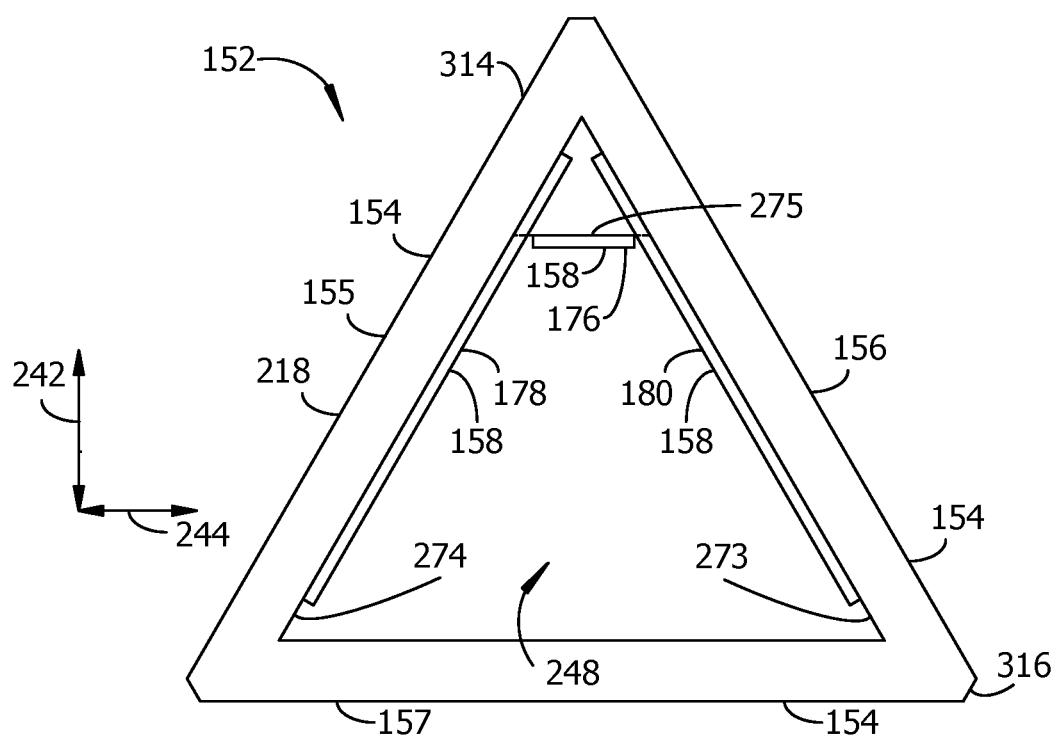
FIG. 20 is an end view of another example triangular pressure transducer with three pressure sensors.
Figure 21:
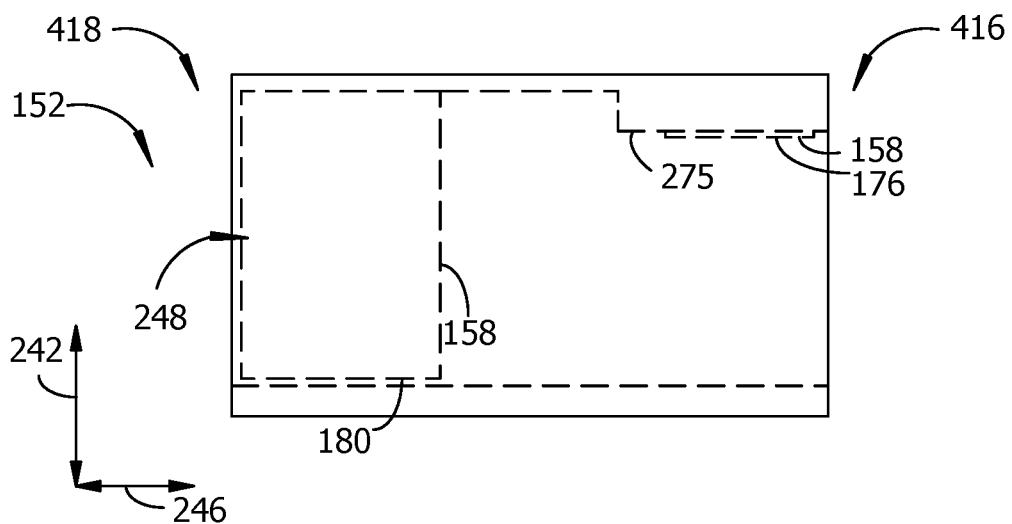
FIG. 21 is a side view of the example triangular pressure transducer of FIG. 20.

An alternative embodiment of a triangular pressure transducer 152, for example as shown in FIG. 20 and FIG. 21, includes a hollow support frame 218 formed as a hollow triangular structure 314, with a first transducer side wall 155 joined to a second transducer side wall 156 and a third transducer side wall 157 attached to the first and second transducer side walls. The three transducer side walls surround a transducer void space 248 extending from a first end of the triangular pressure transducer to a second end opposite the first end. The hollow support frame 218 is formed with a sensor mounting surface 275 within the transducer void space 248. The sensor mounting surface 275 is formed flat and parallel to the third transducer side wall 157 and extends from the first transducer side wall 155 to the second transducer side wall 156 on a side of the transducer void space 248 opposite the third transducer side wall 157.

The example triangular pressure transducer 152 of FIG. 20 and FIG. 21 includes at least one and optionally three pressure sensors 158. A first pressure sensor 176 is attached to the sensor mounting surface 275 near the inboard end 416. An optional second pressure sensor 178 is attached to a flat surface 274 formed on the first transducer side wall 155 inside the transducer void space 248. The optional second pressure transducer 178 is preferably positioned near the outboard end 418 of the triangular pressure transducer, sufficiently close to the outboard end to reliably detect a flexible line being pulled upward relative to the third transducer side wall 157 along the bottom side of the triangular pressure transducer. An optional third pressure sensor 180 is attached to a flat surface 273 formed on the second transducer side wall 156 inside the transducer void space. Like the second pressure transducer 178, the third pressure transducer 180 is preferably positioned near the outboard end 418. The example triangular pressure transducer 152 of FIG. 20 and FIG. 21 is preferably installed in a base unit 110 with the sensor mounting surface 275 holding the first pressure sensor 176 parallel to the enclosure bottom panel 368.

Each flat pressure sensor 158 preferably extends far enough along the wall to which the sensor is attached that an extendable line 114 line pulled toward a wall of the triangular pressure transducer must contact the sensor attached to the wall. The pressure sensors 158 may be have different length, width, and/or thickness dimensions relative to the features of the triangular pressure transducer than the examples in the figures.

For an automatic line reel 100 positioned with the enclosure bottom panel 368 adjacent and parallel to a horizontal surface 286 such as the floor of a room, for example as shown in FIG. 18, the example triangular pressure sensor 152 of FIGS. 20-21 is effective for rapidly and reliably detecting contact pressure exerted by an extendable line 114 pulled in a vertical direction 242 from the horizontal surface and upward and outward from the automatic line reel 100. As with the other triangular pressure sensor embodiments 152 disclosed herein, the example triangular pressure sensor 152 of FIGS. 20-21 is further effective for rapidly and reliably detecting contact pressure exerted by an extendable line 114 passing in a longitudinal direction 246 through the transducer void space 248 while being pulled in transverse directions 244.

The first pressure sensor 176 in the example of FIG. 20 and FIG. 21 is positioned to detect when the extendable line has become over-extended, threatening detachment of the extendable line from the reel assembly or damage to the extendable line. The extendable line unwinds from the reel assembly until the tension in the line caused by an external pull against the line causes the line segment between the reel assembly and the triangular pressure transducer to pull upward and toward the first pressure sensor 176, eventually contacting the first pressure sensor with sufficient force to activate a response from the sensor. Activation of the first pressure sensor 176 preferably causes a rapid halt to rotation of the reel assembly. In some embodiments 100, after activation of the first pressure sensor 176 halts rotation of the reel assembly, thereby halting extension of the extendable line, the processor 166 (ref. FIG. 14) directs the motor 160 to rotate in the opposite direction for a time duration sufficient to rewind one or two turns of the extendable line onto the reel drum 140.

The second pressure sensor 178 and third pressure sensor 180 are positioned at or near the outboard end 418 to detect tension induced deliberately in the line by a person using the automatic line reel 100. The person may, for example, deliberately give a first pull against the extendable line to command the automatic line reel to extend more line. A second deliberate pull against the line may optionally be interpreted by the processor as an instruction to retract the extendable line.

The example embodiments of an automatic line reel 100 described in FIGS. 1-19 position the axis of rotation 214 of the reel hub 124 for the reel assembly 144 in a transverse direction 244, parallel to the bottom panel 368 of the base unit 110 and with the reel flanges 142 perpendicular to the bottom panel. A reel assembly may alternatively be positioned with the axis of rotation of the reel hub perpendicular to the bottom panel of the base unit and the reel flanges parallel to the bottom panel, as suggested in the example automatic line reel 100 of FIG. 22 and FIG. 23.

Figure 22:
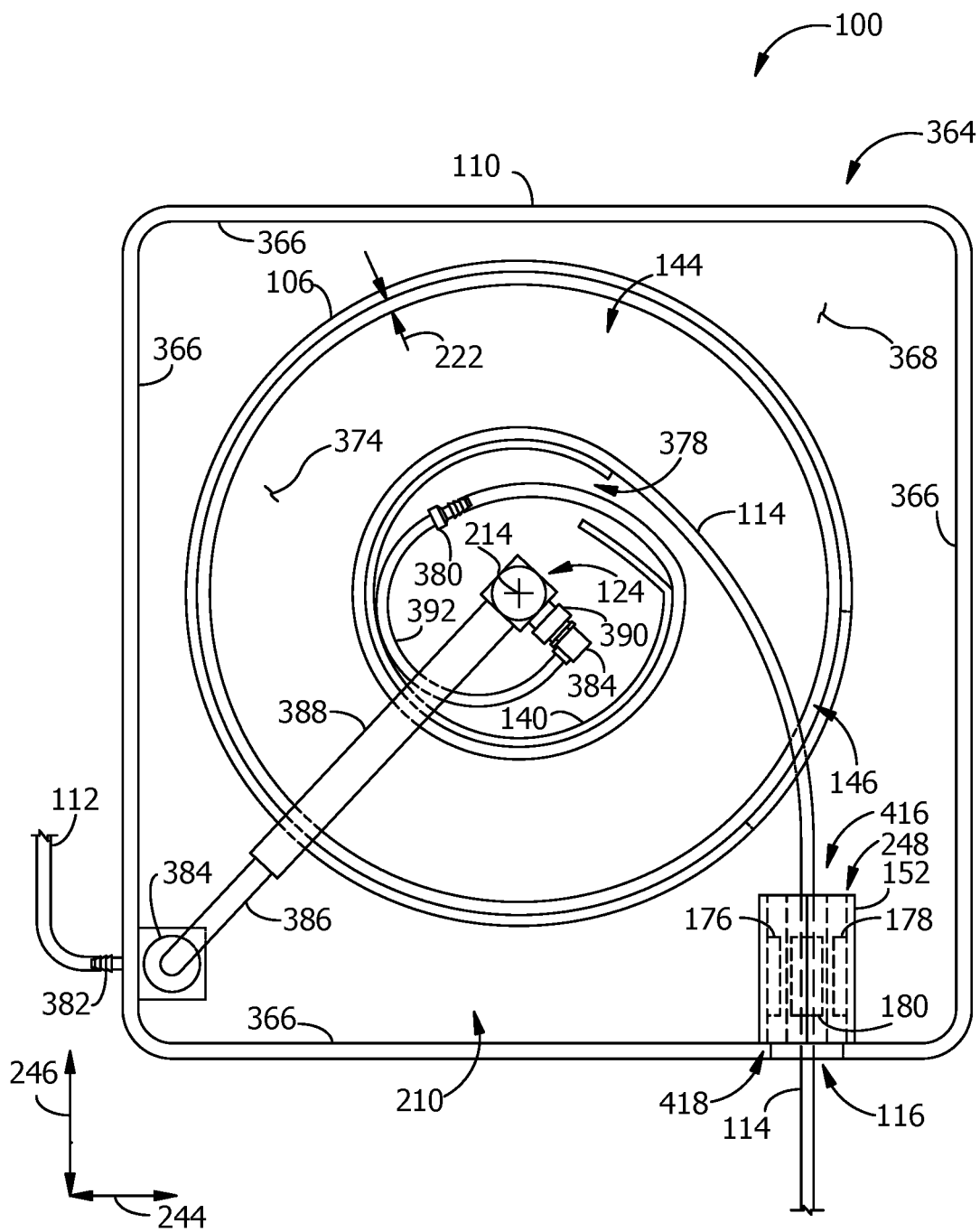
FIG. 22 is a view downward toward another example automatic line reel having the top cover of an outer enclosure removed to show another example reel assembly, the triangular pressure transducer of FIGS. 20-21, and some other components located inside the enclosure.
Figure 23:
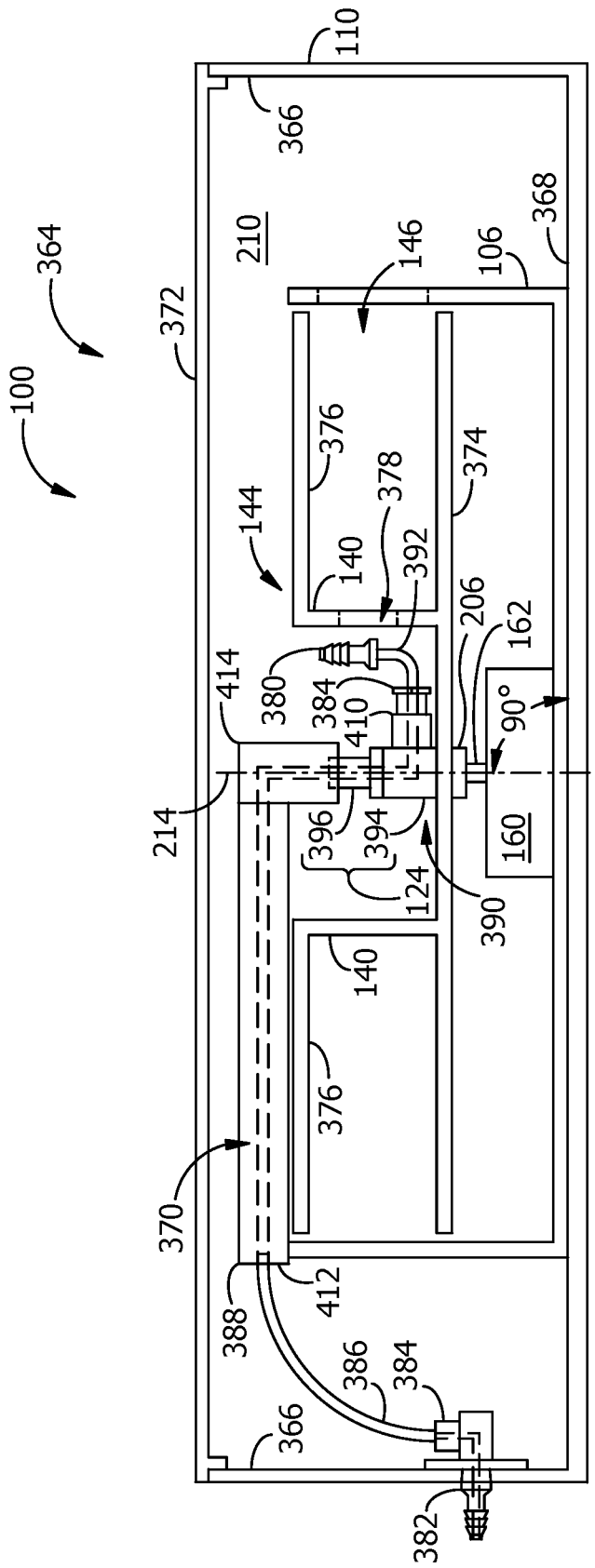
FIG. 23 is a schematic diagram represented as a view toward a side of the example automatic line reel of FIG. 22, showing simplified representations of an example reel assembly and some other components located inside the enclosure of the automatic line reel.

FIG. 22 shows a schematic representation of a view downward into an interior space 210 within four enclosure side walls 366 extending upward from an enclosure bottom panel 368 of a base unit 110 for an example outer enclosure 364 of an automatic line reel 100. FIG. 23 shows a schematic representation of a side view into the interior space 210 within the side walls 366, bottom panel 368, and enclosure cover 372 of the example outer enclosure 364. As for all the embodiments of an automatic line reel 100 disclosed herein, the speed of rotation of the reel assembly by the motor changes in response to activation of the triangular pressure transducer, in some operational situations stopping rotation of the reel assembly and in other operational situations rotating the reel assembly to wind or unwind the extendable line from the reel assembly. Electrical components and operational features of the example automatic line reel 100 of FIG. 22 and FIG. 23 are in accord with FIG. 14 and FIG. 15. The reel assembly may optionally be used with the example line stops described previously for FIG. 18 and FIG. 19.

The enclosure cover 372 is removably attached to the four enclosure side walls 366. In FIG. 22, the enclosure cover has been removed to show examples of some components positioned inside the base unit 110, including the reel assembly 144, the triangular pressure transducer 152, and components for providing a continuous, gas-tight flow path from a stationary line 112 making a gas-tight connection to a tubing connector 382, through a stationary 90° pipe elbow connected to a reel hub 124 for the reel assembly 144, to a tubing connector 380 configured for gas-tight connection to a readily replaceable extendable line 114. A gas-tight connection does not leak a gas such as air or oxygen through the mechanical interface between the connected components. The tubing connector 380 for connection to an extendable line may be referred to as a first tubing connector. The tubing connector 382 for connection to a stationary line may be referred to as a second tubing connector.

The reel assembly 144 stores loops of the extendable line 114 on the reel drum 140. The reel assembly 144 is positioned within a fixed reel cover 106 attached to or alternately formed as an integral part of the enclosure bottom panel 368. The fixed reel cover 106 is stationary relative to the outer enclosure 364 and is provided to separate rotating components from nonrotating components inside the enclosure and to contain loops of the extendable line wound around the reel drum. A gap 222 between the fixed reel cover 106 and the flange or flanges of the reel assembly is preferably large enough to prevent contact between the rotatable reel assembly and fixed reel cover and small enough to prevent the extendable line 114 from becoming trapped or pinched between the reel assembly and fixed reel cover.

The reel assembly includes a lower reel flange 374 joined to the reel drum 140 and optionally includes an upper reel flange 376 joined to the reel drum. The example reel assembly 144 in FIG. 22 includes the bottom flange 374 but omits the optional top flange 376. The reel drum 140 is formed with a slot or aperture 378 to enable a removable connection to be formed between an end of the extendable line 114 and the tubing connector 380 positioned within a space inside the reel drum 140. Starting from the exterior of the automatic line reel 100, the extendable line 114 passes through the line aperture 116 formed in the side wall 366 of the outer enclosure 364, through the outboard end 418 of the triangular pressure transducer 152, though the transducer void space 248 and out the inboard end 416, through an extendable line aperture 146 formed in the fixed reel cover 106, preferably winds for at least one turn around the reel drum 140, and then passes through the slot 378 in the reel drum, where an end of the extendable line is removably attached with a gas-tight connection to a tubing connector 380. Keeping at least one turn of extendable line around the reel drum provides a strain relief for preventing disconnection of the extendable line from the tubing connector 380 in the reel drum.

The example triangular pressure transducer 152 in FIG. 22 and FIG. 23 is in accord with the examples of FIG. 20 and FIG. 21. Alternatively, any of the example configurations of a triangular pressure transducer from FIGS. 8-13, 16, and 17 may be used with the automatic line reel 100 of FIG. 23 and FIG. 24. The example triangular pressure transducer 152 of FIG. 20 and FIG. 21 may optionally be used with any of the example automatic line reel 100 embodiments disclosed herein.

After being attached to the tubing connector 380, the extendable line may be wound and unwound from the reel drum by rotation of the reel assembly. The reel assembly 144 is driven in rotation by the motor 160 having a motor drive shaft 162 engaged with a drive shaft connector 206 attached to or integrally formed with the reel drum 140. The motor is positioned in the base unit 110 with an axis of rotation 214 for the motor drive shaft 162 perpendicular to the enclosure bottom panel 168.

A centerline 214 extending in a vertical direction 246 through the motor drive shaft, reel drum 140, and a reel hub 124 is coincident with an axis of rotation 214 for the reel assembly positioned at an angle of 90° to the enclosure bottom panel 368. The lower reel flange 374 and optional upper reel flange 376 attached to the reel drum 140 extend outward from the drum and radially away from the axis of rotation 214. The example reel assembly 144 of FIG. 22 and FIG. 23 rotates with the lower reel flange 374 in a plane parallel to the enclosure back panel and perpendicular to the axis of rotation 214. In comparison to the example automatic line reel 100 of FIG. 22 and FIGS. 23, the alternative embodiment 100 in the examples illustrated in FIGS. 1-7, 18, and 19 has the axis of rotation 214 for the reel assembly parallel to the enclosure bottom panel 368 and the reel assembly rotates with the reel flanges perpendicular to the enclosure bottom panel.

A continuous, uninterrupted flow path 370 for leak-free transport of a gas and/or liquid is provided from the tubing connector 382 fixed to the enclosure side wall 366 to the tubing connector 380 in the reel drum 140. Beginning at the tubing connector 382 for the stationary line 112, the flow path 370 passes through a first hollow tube 386 attached with a gas-tight connection to the tubing connector 382 by a first tubing connector 384. The first hollow tube 386 connects to a rigid, stationary 90° pipe elbow 388 positioned above the fixed reel cover 106 or alternately to a bracket or other structure that remains stationary with respect to the outer enclosure 364. The stationary 90° pipe elbow 388 includes a hollow elongated segment 412 and a hollow short segment 414 extending at a right angle to and in fluid communication with the elongate segment. The short segment 414 of the 90° pipe elbow 388 connects to the reel hub 124, holding part of the reel hub stationary as other parts of the reel hub rotate with the reel assembly. The example elongated segment 412 is sufficiently long to reach from the short segment 414 to the fixed reel cover 106. The elongated segment 412 is held stationary relative to the fixed reel cover by being attached to the reel cover, by a bracket (not illustrated), or by the first hollow tube 386 optionally being formed from a rigid material.

An end of the short segment 414 of the stationary 90° pipe elbow 388 connects with a gas-tight connection to the reel hub 124. The reel hub 124 in some embodiments 100 includes a 90° swivel union 390. The stationary 90° pipe elbow 388 connects to a first swivel union tube 396 that is part of the 90° swivel union 390. The first swivel union tube 396 is coupled with a gas-tight rotatable joint to a swivel union block 394 forming another part of the swivel union 390. The first swivel union tube 396 does not rotate with the reel assembly and may therefore also be referred to as a stationary swivel union tube 396. The swivel union block 394 is strongly attached to the reel drum 140, rotating with the reel drum as the reel assembly turns while maintaining a gas-tight connection to the stationary swivel union tube 396. The flow path 370 continues through the swivel union block 394 to a second swivel union tube 410 joined to the swivel union block 394, then through a second flexible hollow tube 392 connected to the second swivel union tube by a second tubing connector 384. The second flexible hollow tube 392 joins with a gas-tight connection to the tubing connector 380 for the extendable line. An end of the extendable line 114 passes through the aperture 378 in the reel drum to connect to the tubing connector 380.

The swivel union block 394, second swivel union tube 410, second flexible hollow tube 392, tubing connector 380, reel drum 140, and reel flange(s) rotate together about the central axis of rotation 214 of the reel hub 124 when the extendable line 114 is being wound or unwound from the reel assembly by operation of the motor 160. The first swivel union tube 396, elongated segment 412 and short segment 414 of the stationary 90° pipe elbow 388, first hollow tube 386, and the tubing connector 382 for the stationary line 112 remain stationary relative to the outer enclosure 364 during rotation of the reel assembly 144. The first hollow tube is made from a flexible material in some embodiments and from a rigid material in other embodiments.

In the examples of FIG. 22 and FIG. 23, the first tubing connector 380 and the second tubing connector 382 are provided with hose barbs for attachment of the extendable line 114 and stationary line 112. The first tubing connector may alternately be a different type of connector than the second tubing connector. The first and second connectors may alternately form connections to the extendable line and stationary line by a means other than hose barbs, for example swaged connections, threaded fittings, and other commonly available connectors for tubing and hose.

Figure 24:
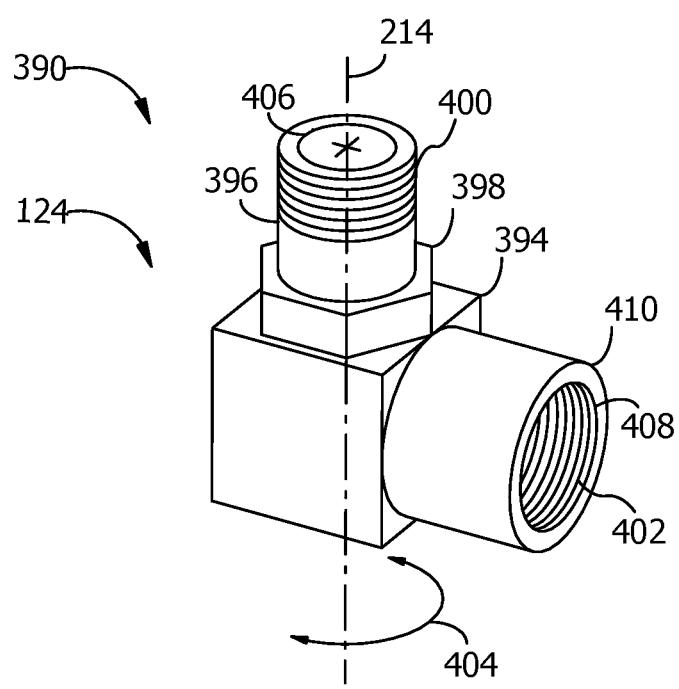
FIG. 24 is a pictorial view of an example 90° swivel union forming part of the reel hub in the example automatic line reel of FIGS. 22-23.

Some features of an example 90° swivel union 390 suitable for use with a reel hub 124 in the example automatic line reel 100 of FIG. 22 and FIG. 23 are shown in FIG. 24. The first swivel union tube 396 rotatably couples with a gas-tight connection to the swivel union block 394. An aperture 408 in the second swivel union tube 410 is in fluid communication with an aperture 406 in the first swivel union tube through apertures (not shown) in the intervening swivel union block. The swivel union block 394 is rotatable in either direction 404 relative to the first swivel union tube 396 about an axis of rotation 214. An optional hex flange 398 formed on the first swivel union tube 396 facilitates tightening the first swivel union tube into the short segment 414 of the stationary 90° pipe elbow 388. In the illustrated example, an external thread 400 is formed on the first swivel union tube 396 and an internal thread 402 is formed in the aperture through the second swivel union tube 410, but other threading arrangements may be used. The swivel union block 394 of the reel hub 124 will preferably be attached to the reel drum 140 of the reel assembly 144 with the axis of rotation 214 of the reel hub 124 coincident with the axis of rotation 214 of the 90° swivel union 390.

Unless expressly stated otherwise herein, ordinary terms have their corresponding ordinary meanings within the respective contexts of their presentations, and ordinary terms of art have their corresponding regular meanings.

What is claimed is:

1. An apparatus, comprising:
   an outer enclosure having a bottom panel;
   a motor comprising a motor drive shaft rotatable about an axis of rotation, said motor attached to said outer enclosure with said axis of rotation perpendicular to said bottom panel;
   a reel assembly, comprising:
      a reel drum configured for connection to said motor drive shaft;
      a reel flange attached to said reel drum, said reel flange extending radially outward from said axis of rotation;
      a reel hub attached to said reel drum, said reel hub comprising a stationary swivel union tube and a swivel union block rotatably joined to said stationary swivel union tube, said swivel union block attached to said reel drum, and said reel drum, said reel flange, and said swivel union block rotatable together about said axis of rotation by said motor; and a triangular pressure transducer attached to said outer enclosure, comprising:
  a first transducer side wall;
  a second transducer side wall joined to said first transducer side wall;
  a third transducer side wall joined to said first transducer side wall and said second transducer side wall with a transducer void space formed between said first transducer side wall, said second transducer side wall, and said third transducer side wall;
  a sensor mounting surface extending from said first transducer side wall to said second transducer side wall; and
  a pressure sensor attached to said sensor mounting surface, wherein a speed of rotation of said reel assembly by said motor changes in response to activation of said triangular pressure transducer.

2. The apparatus of claim 1, where said triangular pressure transducer is positioned in said outer enclosure with said sensor mounting surface parallel to said bottom panel.

3. The apparatus of claim 1, said triangular pressure transducer further comprising:
  a second pressure sensor attached to said first transducer side wall inside said transducer void space; and
  a third pressure sensor attached to said second transducer side wall inside said transducer void space.

4. The apparatus of claim 1, further comprising:
  a first tubing connector connected for fluid communication with said swivel union block;
  a second tubing connector attached to said outer enclosure;
  a stationary pipe elbow, comprising:
    a hollow elongated segment connected for fluid communication with said second tubing connector; and
    a hollow short segment extending at a right angle from said elongated segment, said short segment connected for fluid communication with said swivel union tube, wherein said stationary pipe elbow holds said stationary swivel union tube stationary with respect to said outer enclosure, and said first tubing connector is connected for fluid communication with said second tubing connector through said stationary pipe elbow, said swivel union tube, and said swivel union block.

5. The apparatus of claim 4, further comprising a fixed reel cover formed with an extendable line aperture, said fixed reel cover attached to said bottom panel inside said enclosure, and said reel assembly positioned inside said reel cover.

6. The apparatus of claim 5, further comprising said reel drum formed with an aperture positioned to admit an extendable line.

7. The apparatus of claim 6, further comprising an extendable line passing through said transducer void space, said extendable line aperture in said reel cover, and said aperture in reel drum, said extendable line connected for fluid communication with said first tubing connector.

8. An apparatus, comprising:
an outer enclosure having a bottom panel, four side walls extending upward from said bottom panel, and an enclosure cover removably attached to said side walls;
a reel cover attached to said bottom panel in a space between said side walls, said bottom panel, and said enclosure cover;
a motor having a motor drive shaft rotatable about an axis of rotation, said motor attached to said outer enclosure with said axis of rotation perpendicular to said bottom panel;
a reel assembly positioned within reel cover, comprising:
  a reel drum configured for connection to said motor drive shaft;
  a reel flange attached to said reel drum, said reel flange extending radially outward from said axis of rotation;
  a reel hub attached to said reel drum, said reel hub comprising a stationary swivel union tube held stationary relative to said outer enclosure and a swivel union block rotatably joined to said stationary swivel union tube, said swivel union block attached to said reel drum, and said reel drum, said reel flange, and said swivel union block rotatable together about said axis of rotation by said motor; and
a triangular pressure transducer attached to said outer enclosure in said space between said four walls, comprising:
  a first transducer side wall;
  a second transducer side wall joined to said first transducer side wall;
  a third transducer side wall joined to said first transducer side wall and said second transducer side wall with a transducer void space formed between said first transducer side wall, said second transducer side wall, and said third transducer side wall;
  a sensor mounting surface formed parallel to said third transducer side wall inside said transducer void space opposite said third transducer side wall, said sensor mounting surface extending from said first transducer side wall to said second transducer side wall; and
  a pressure sensor attached to said sensor mounting surface.

9. An apparatus, comprising:
an outer enclosure having a bottom panel;
a motor comprising a motor drive shaft rotatable about an axis of rotation, said motor positioned inside said outer enclosure with said axis of rotation perpendicular to said bottom panel;
a reel assembly, comprising:
  a reel drum configured for connection to said motor drive shaft;
  a reel flange attached to said reel drum, said reel flange extending radially outward from said axis of rotation;
  a reel hub attached to said reel drum, said reel hub comprising a swivel union having a first end held stationary relative to said enclosure and a second end attached to said reel drum, and said reel drum, said reel flange, and said second end of said swivel union rotatable together about said axis of rotation by said motor; and
a triangular pressure transducer attached to said outer enclosure, comprising:
  a first transducer side wall;
  a second transducer side wall joined to said first transducer side wall;
  a third transducer side wall joined to said first transducer side wall and said second transducer side wall with a transducer void space formed between said first transducer side wall, said second transducer side wall, and said third transducer side wall;

a sensor mounting surface formed parallel to said third transducer side wall and extending from said first transducer side wall to said second transducer side wall; and
a pressure sensor attached to said sensor mounting surface.

\* \* \* \* \*